United States Patent
Jiao et al.

(10) Patent No.: US 11,230,750 B2
(45) Date of Patent: *Jan. 25, 2022

(54) ENGINEERED MICROBES FOR RARE EARTH ELEMENT ADSORPTION

(71) Applicants: Lawrence Livermore National Security, LLC, Livermore, CA (US); Battelle Energy Alliance, LLC, Idaho Falls, ID (US)

(72) Inventors: Yongqin Jiao, Pleasanton, CA (US); Dan McFarland Park, Dublin, CA (US); Mimi Cho Yung, Milpitas, CA (US); David W. Reed, Idaho Falls, ID (US)

(73) Assignees: Lawrence Livermore National Security, LLC, Livermore, CA (US); Battelle Energy Alliance, LLC, Idaho Falls, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/229,853

(22) Filed: Dec. 21, 2018

(65) Prior Publication Data

US 2019/0119778 A1 Apr. 25, 2019

Related U.S. Application Data

(63) Continuation of application No. 15/400,948, filed on Jan. 6, 2017, now Pat. No. 10,196,708.

(51) Int. Cl.
| | | |
|---|---|---|
| *C22B 3/18* | (2006.01) | |
| *C12P 3/00* | (2006.01) | |
| *C07K 14/195* | (2006.01) | |
| *C22B 59/00* | (2006.01) | |
| *C07K 14/47* | (2006.01) | |

(52) U.S. Cl.
CPC .............. *C22B 3/18* (2013.01); *C07K 14/195* (2013.01); *C07K 14/4716* (2013.01); *C07K 14/4728* (2013.01); *C12P 3/00* (2013.01); *C22B 59/00* (2013.01); *C07K 2319/20* (2013.01); *C07K 2319/60* (2013.01); *Y02P 10/20* (2015.11)

(58) Field of Classification Search
None
See application file for complete search history.

(56) References Cited

U.S. PATENT DOCUMENTS

| | | | |
|---|---|---|---|
| 4,683,196 A | 7/1987 | McLaughlin | |
| 5,512,435 A | 4/1996 | Renschler et al. | |
| 10,196,708 B2* | 2/2019 | Jiao | C07K 14/4728 |
| 2003/0228622 A1 | 12/2003 | Imperiali et al. | |
| 2018/0195147 A1 | 7/2018 | Jiao et al. | |
| 2020/0048732 A1 | 2/2020 | Barker et al. | |

FOREIGN PATENT DOCUMENTS

| | | |
|---|---|---|
| WO | 2015111407 A1 | 7/2015 |
| WO | 2017136561 A1 | 8/2017 |

OTHER PUBLICATIONS

Martin et al. Double-Lanthanide-Binding Tags: Design, Photophysical Properties, and NMR Applications, JACS, 2007, 129, 7106-7113.*
Moriwaki et al., Interactions of microorganisms with rare earth ions and their utilization for separation and environmental technology, Appl Microbiol Biotechnol (2013) 97:1-8.*
Lee et al., Microbial cell-surface display, TRENDS in Biotechnology vol. 21 No. 1 Jan. 2003.*
Ryan, Highly Sensitive Method for Detecting and Separating Pathogens using Paramagnetic Particles and a Micro-Fluidic System, Apr. 2013 Department of Biomedical Engineering.*
Cotton, S., "Lanthanide and Actinide Chemistry", John Wiley & Sons Ltd, 2006, 267 pages.
Cox, S., J., et al., "Characterizing Heterogeneous Bacterial Surface Functional Groups Using Discrete Affinity Spectra for Proton Binding" Department of Geology, Environmental Science & Technology, vol. 33, No. 24, 1999, 8 pages.
Dent, C., P., "Rare earth elements and permanent magnets (invited)", Journal of Applied Physics, Mar. 2012, 7 pages.
Gadd, M., G., "Biosorption: critical review of scientific rationale, environmental importance and significance for pollution treatment", Society of Chemical Industry, Jul. 2008, 16 pages.
Gupta, K., C., "Extractive Metallurgy of Rare Earths", CRC Press, 2005, 484 pages.
Hansel, M., C., "Coupled Photochemical and Enzymatic Mn(II) Oxidation Pathways of a Planktonic Roseobacter-Like Bacterium", American Society for Microbiology, Feb. 2006, 7 pages.
Hosomomi, Y., et al., "Biosorption of Rare Earth Elements by *E. coli*", Journal of Chemical Engineering of Japan, Jun. 2013, 22 pages.
Humphries, M., "Rare Earth Elements: The Global Supply Chain", Congressional Research Services, Dec. 2013, 31 pages.
Kazy, K. S., et al., "Lanthanum biosorption by a *Pseudomonas* sp.: equilibrium studies and chemical characterization", Society for Industrial Microbiology, Apr. 2006, 11 pages.
Kelly, D., S., et al., "X-ray absorption fine structure determination of pH-dependent U-bacterial cell wall interactions", Geochimica et Cosmochimica Acta, vol. 66, No. 22, Apr. 2002, 17 pages.
Kotrba, P., "Microbial Biosorption of Metals", Springer Science and Business Media B.V., 2011, 334 pages.
Markai, S., "Study of the interaction between europium (III) and *Bacillus subtilis*: fixation sites, biosorption modeling and reversibility", Journal of Colloid and Interface Science 262 (2003) 351-361.
Ngwenya, T., B., et al., "Macroscopic and spectroscopic analysis of lanthanide adsorption to bacterial cells", Geochimica et Cosmochimica Acta 73 (2009) 3134-3147.

(Continued)

*Primary Examiner* — Channing S Mahatan
(74) *Attorney, Agent, or Firm* — Perkins Coie LLP

(57) ABSTRACT

Presently described are engineered microbes modified such that the surface of the microbe contains one or more rare earth element (REE) binding ligands, as well as methods of use thereof.

19 Claims, 17 Drawing Sheets

Specification includes a Sequence Listing.

(56) References Cited

OTHER PUBLICATIONS

Park, M., D., "Recovery of Rare Earth Elements from Low-Grade Feedstock Leachates Using Engineered Bacteria", Environmental Science & Technology, 2017, 51, 10 pages.

Takahashi, Y., "EXAFS study on the cause of enrichment of heavy REEs on bacterial cell surfaces", Geochimica et Cosmochimica Acta 74 (2010) 5443-5462.

Takahashi, Y., et al. "Adsorption of rare earth elements onto bacterial cell walls and its implication for REE sorption onto natural microbial mats", Chemical Geology 219 (2005) 53-67.

Texier, A., et al., "Characterization of Lanthanide Ions Binding Sites in the Cell Wall of *Pseudomonas aeruginosa*", Environ. Sci. Technol. 2000, 34, 610-615.

U.S. Department of Energy, "Critical Materials Strategy", Dec. 2011, 196 pages.

Vogel, C., "Metal accumulation by heterotrophic marine bacterioplankton", Limnol. Oceanogr., 55(2), 2010, 519-528.

Abate, A.R., et al., "High-Order Multiple Emulsions Formed in Poly(dimethylsiloxane) Microfluidics," Small Journal, 5(18):2030-2032, Sep. 2009.

Acerce, M., et al., "Metallic 1T phase M0S$_2$ nanosheets as supercapacitor electrode materials," Nature Nanotechnology, 10(4):313-318, Mar. 2015.

Allen, K.N., et al., "Lanthanide-tagged proteins—an illuminating partnership," Current Opinion in Chemical Biology, 14(2):247-254, Apr. 2010.

Anastopoulos, I. B., A.; Lima, E. C., Adsorption of rare earth metals: A review of recent literature. Journal of Molecular Liquids 2016, 221, 954-962.

Bayer, M.E., et al., "Lanthanide Accumulation in the Periplasmic Space of *Escherichia coli* B," Journal of Bacteriology, 173(1):141-149, Jan. 1991.

Binnemans, K., et al., "Recycling of rare earths: a critical review," Journal of Cleaner Production, 51:1-22, Jul. 2013.

Bonificio, W., et al., "Rare-Earth Separation Using Bacteria Environ" Sci Technol Lett 2016, 3 180-184.

Doe, Critical Materials Strategy. In 2011.

Entcheva-Dimitrov, P., et al., "Dynamics and Control of Biofilms of the Oligotrophic Bacterium Caulobacter crescentus," Journal of Bacteriology, 186(24):8254-8266, Dec. 2004.

Fujita, Y., et al., "Effects of Simulated Rare Earth Recycling Wastewaters on Biological Nitrification," Environmental Science & Technology, 49(16):9460-9468, Jul. 2015.

Gadd, G.M., "Metals, minerals and microbes: geomicrobiology and bioremediation," Microbiology, 156(3):609-643, Mar. 2010.

Gomes, H.I., et al., "Alkaline residues and the environment: a review of impacts, management practices and opportunities," Journal of Cleaner Production, 112(4):3571-3582, Jan. 2016.

Goyne, K.W., et al., "Rare earth element release from phosphate minerals in the presence of organic acids," Chemical Geology, 278(1-2):1-14, Nov. 2010.

Herrera, C.M., et al., "Activation of PmrA inhibits LpxT-dependent phosphorylation of lipid A promoting resistance to antimicrobial peptides," Molecular Microbiology, 76(6):1444-1460, Apr. 2010.

Martin, L.J., et al., "Double-Lanthanide-Binding Tags: Design, Photophysical Properties, and NMR Applications," Journal of the American Chemical Society, 129(22):7106-7113, May 2007.

McDonald, J.C., et al., "Poly(dimethylsiloxane) as a Material for Fabricating Microfluidic Devices," Accounts of Chemical Research, 35(7):491-499, Apr. 2002.

McGill, I., "Rare Earth Elements", In Ullman's Encyclopedia of Industrial Chemistry, Wiley-VCH: Weinheim, 2000; pp. 183-228.

Moore, E.G., et al., "An Octadentate Luminescent Eu(III) 1,2-HOPO Chelate with Potent Aqueous Stability," Inorganic Chemistry, 46(14):5468-5470, Jul. 2007.

Nomellini, J.F., et al., "S-Layer-Mediated Display of the Immunoglobulin G-Binding Domain of Streptococcal Protein G on the Surface of Caulobacter crescentus: Development of an Immunoactive Reagent," Applied and Environmental Microbiology, 73(10):3245-3253, May 2007.

Ozaki, T., et al., "Sorption Behavior of Europium(III) and Curium(III) on the Cell Surface of Microorganisms," Radiochimica Acta, 92(9-11):741-748, Nov. 2004.

Park, D.M., et al., "Modulation of Medium pH by *Caulobacter crescentus* Facilitates Recovery from Uranium-Induced Growth Arrest," Applied and Environmental Microbiology, 80(18):5680-5688, Sep. 2014.

Park, D.M., et al., "Bioadsorption of Rare Earth Elements through Cell Surface Display of Lanthanide Binding Tags," Environmental Science & Technology, 50(5):2735-2742, Feb. 2016.

Patel, J., et al., "Genetic Engineering of Caulobacter crescentus for Removal of Cadmium from Water," Applied Biochemistry and Biotechnology, 160(1):232-243, Feb. 2009.

Patel, J., et al., "Self-immobilization of Recombinant Caulobacter crescentus and Its Application in Removal of Cadmium from Water," Applied Biochemistry and Biotechnology, 162(4):1160-1173, Jan. 2010.

Peelman, S., et al., "Leaching of rare earth elements: Review of past and present technologies. In Rare Earths Industry Technological, Economic, and Environmental Implications", 1st ed.; Borges de Lima, I. F., W. L., Ed. 2015; pp. 319-334.

Rahimi, Y., et al., "Mechanism of Copper Induced Fluorescence Quenching of Red Fluorescent Protein, DsRed," Biochemical and Biophysical Research Communications, 370(1):57-61, May 2008.

Smit, J., et al., "The S-layer of Caulobacter crescentus: Three-Dimensional Image Reconstruction and Structure Analysis by Electron Microscopy," Journal of Bacteriology, 174(20):6527-6538, Oct. 1992.

Taggart, R.K., et al., "Trends in the Rare Earth Element Content of U.S.-Based Coal Combustion Fly Ashes," Environmental Science & Technology, 50(11):5919-5926, May 2016.

Texier, A.-C., et al., "Selective Biosorption of Lanthanide (La, Eu, Yb) Ions by Pseudomonas Aeruginosa," Environmental Science & Technology, 33(3):489-495, Dec. 1998.

Towett, E.K., et al., "Quantification of Total Element Concentrations in Soils Using Total X-ray Fluorescence Spectroscopy (TXRF)," Science of The Total Environment, 463-464(1):374-388, Jul. 2013.

Utturkar, S.M., et al., "Draft Genome Sequence for *Caulobacter* sp. Strain OR37, a Bacterium Tolerant to Heavy Metals," Genome Announcements, 1(3):1-2, May 2013.

Walker, S.G., et al., "Isolation and Comparison of the Paracrystalline Surface Layer Proteins of Freshwater Caulobacters," Journal of Bacteriology, 174(6):1783-1792, Mar. 1992.

Wang, P., et al., "A Speciation-Based Model for Mixed-Solvent Electrolyte Systems," Fluid Phase Equilibria, 203(1-2):141-176, Dec. 2002.

Wang, P., et al., "Modeling Phase Equilibria and Speciation in Mixed-Solvent Electrolyte Systems: II. Liquid-Liquid Equilibria and Properties of Associating Electrolyte Solutions," Journal of Molecular Liquids, 125(1):37-44, Mar. 2006.

Wu, Z., et al., "Transparent, Conductive Carbon Nanotube Films," Science, 305(5688):1273-1276, Aug. 2004.

Xie, F., et al., "A Critical Review on Solvent Extraction of Rare Earths from Aqueous Solutions," Minerals Engineering, 56(1):10-28, Feb. 2014.

Ye, C., et al., "Ceramic Microparticles and Capsules via Microfluidic Processing of a Preceramic Polymer," Journal of the Royal Society Interface, 7(4): S461-S473, May 2010.

Zhuang, W.-Q., et al., "Recovery of Critical Metals Using Biometallurgy," Current Opinion in Biotechnology, 33(1):327-335, Jun. 2015.

Bunzli, J. C., "Benefiting from the Unique Properties of Lanthanide Ions," Accounts of Chemical Research, 39(1):53-61, Jan. 2006.

Cheng, Y. C., et al., "Relationship between the inhibition constant ($K_1$) and the concentration of inhibitor which causes 50 per cent inhibition ($I_{50}$) of an enzymatic reaction," Biochemical Pharmacology, 22(23):3099-3108, Dec. 1973.

Chi, R., et al., "A solution chemistry approach to the study of rare earth element precipitation by oxalic acid," Metallurgical and Materials Transactions B, 30(2):189-195, Apr. 1999.

(56) References Cited

OTHER PUBLICATIONS

Daumann, L.J., et al., "Siderophore inspired tetra- and octadentate antenna ligands for luminescent Eu(III) and Tb(III) complexes," Journal of Inorganic Biochemistry, 162:263-273, Sep. 2016.

Eggert, et al., "Rare Earths: Market disruption, innovation, and global supply chains," Annu. Rev. Environ. Resour. 2016, 41, 199-222.

Firsching, F.H., et al., "Solubility Products of the Trivalent Rare-Earth Phosphates," Journal of Chemical & Engineering Data, 36(1):93-95, Jan. 1991.

Franz, K.J., et al., "Lanthanide-Binding Tags as Versatile Protein Coexpression Probes," Chembiochem, 4(4):265-271, Apr. 20.

Hennebel, T., et al., "Biotechnologies for critical raw material recovery from primary and secondary sources: R&D priorities and future perspectives," New Biotechnology, 32(1):121 -127, Jan. 2015.

Hutner, S.H., et al., "Some Approaches to the Study of the Role of Metals in the Metabolism of Microorganisms," Proceedings of the American Philosophical Society, 94(2):152-170, Apr. 1950.

Jiang, M.Y., et al., "Post-adsorption process of Yb phosphate nano-particle formation by Saccharomyces cerevisiae," Geochimica et Cosmochimica Acta, 93:30-46, Sep. 2012.

Kuroda, K., et al., "Engineering of microorganisms towards recovery of rare metal ions," Applied Microbiology and Biotechnology, 87(1):53-60, Jun. 2010.

Lo, Y.C., et al., "Recovery of High-Value Metals from Geothermal Sites by Biosorption and Bioaccumulation," Bioresource Technology, 160:182-190, May 2014.

Moriwaki, H., et al., "Interactions of Microorganisms with Rare Earth Ions and their Utilization for Separation and Environmental Technology," Applied Microbiology and Biotechnology, 97(1):1-8, Jan. 2013.

Nitz, M., et al., "Structural Origin of the High Affinity of a Chemically Evolved Lanthanide-Binding Peptide," Angewandte Chemie International Edition, 43(28):3682-3685, Jul. 2004.

Onishi, H., et al., "Spectrophotometric determination of zirconium, uranium, thorium and rare earths with arsenazo III after extractions with thenoyltrifluoroacetone and tri-n-octylamine," Taianta, 19(4):473-478, Apr. 1972.

Parhi, P.K., et al., "Liquid-liquid Extraction and Separation of Total Rare Earth (RE) Metals from Polymetallic Manganese Nodule Leaching Solution," Journal of Rare Earths, 33(2):207-213, Feb. 2015.

Tsuruta, T., "Accumulation of Rare Earth Elements in Various Microorganisms," Journal of Rare Earths, 25(5):526-532, Oct. 2007.

Utada, A.S., et al., "Monodisperse Double Emulsions Generated from Microcapillary Device," Science, 308(5721):537-541, Apr. 2005.

Wei, W., et al., "Simple Whole-Cell Biodetection and Bioremediation of Heavy Metals Based on an Engineered Lead-Specific Operon," Environmental Science & Technology, 48(6):3363-3371, Feb. 2014.

Wu, S., et al., "Preparation and Thermal Behaviour of Rare Earth Citrate Hydrates," Journal of Thermal Analysis, 45(1-2):199-206, Jul. 1995.

* cited by examiner

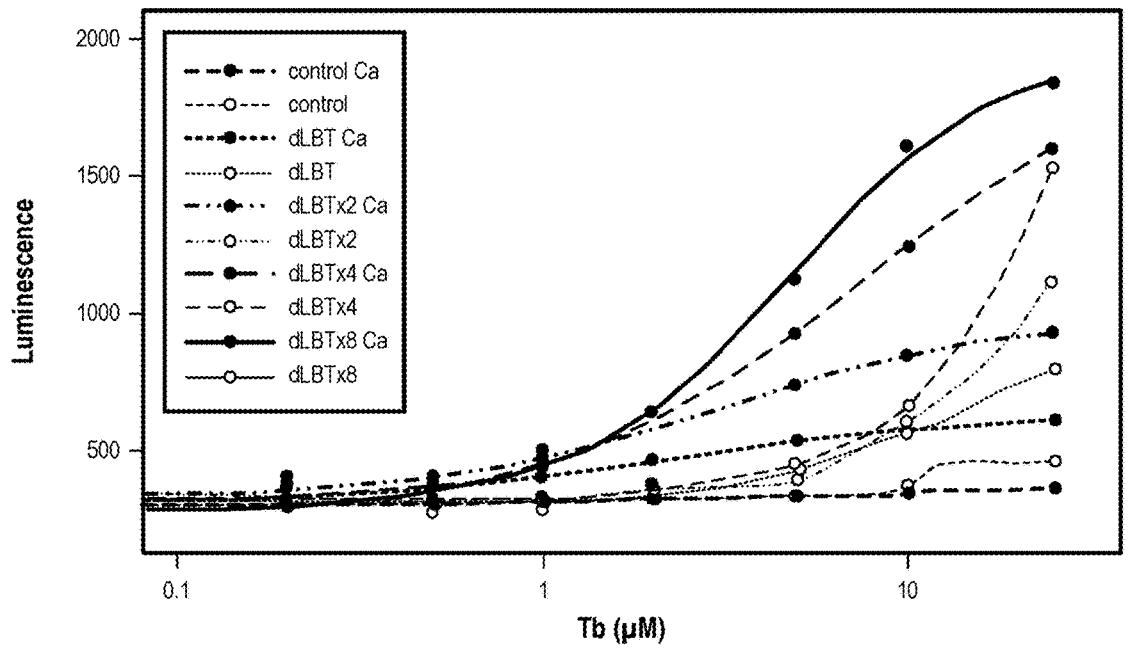
FIG. 2D
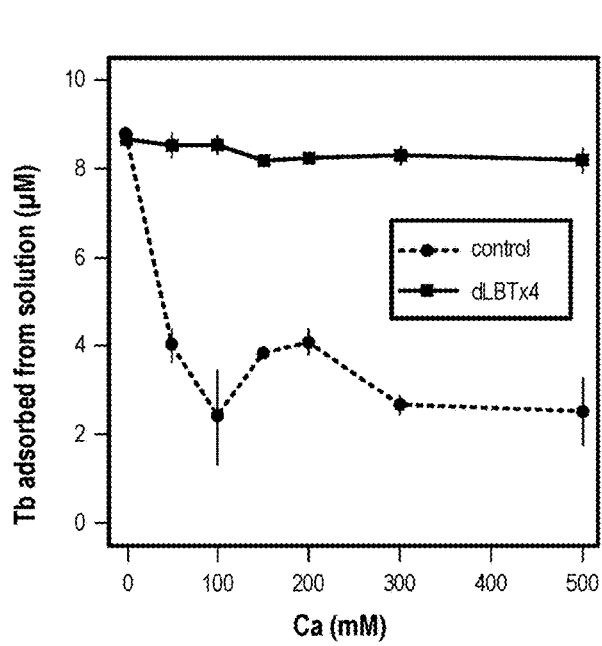 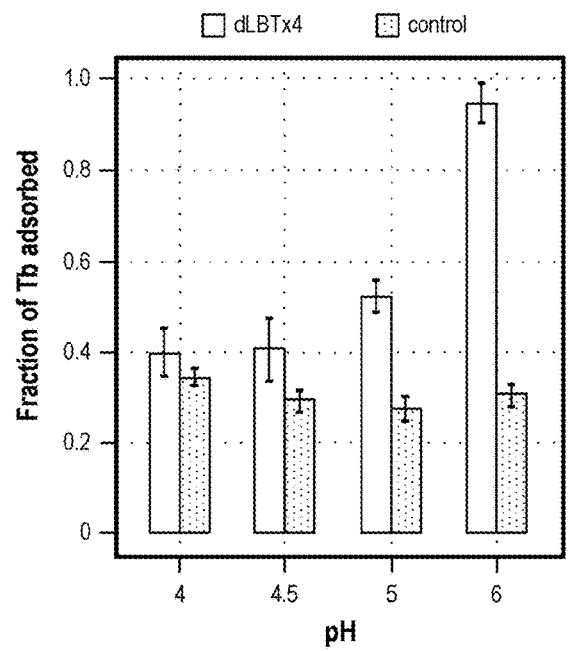
FIG. 2E        FIG. 2F

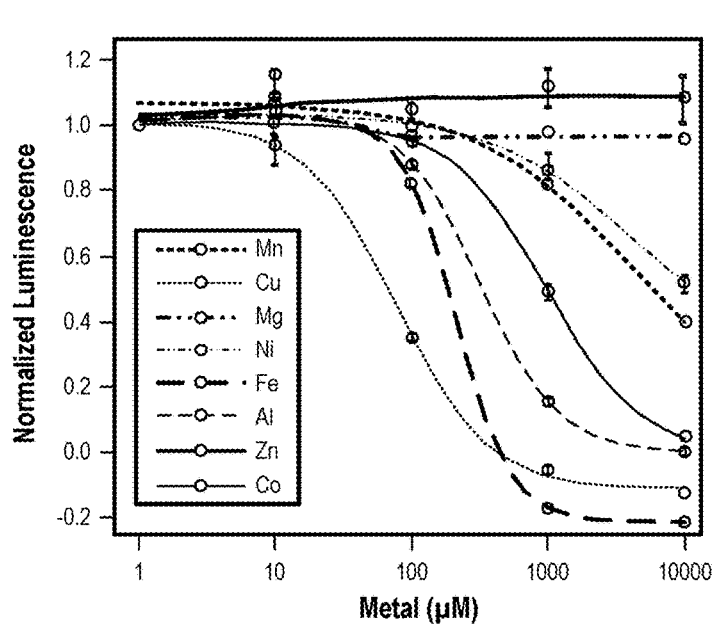 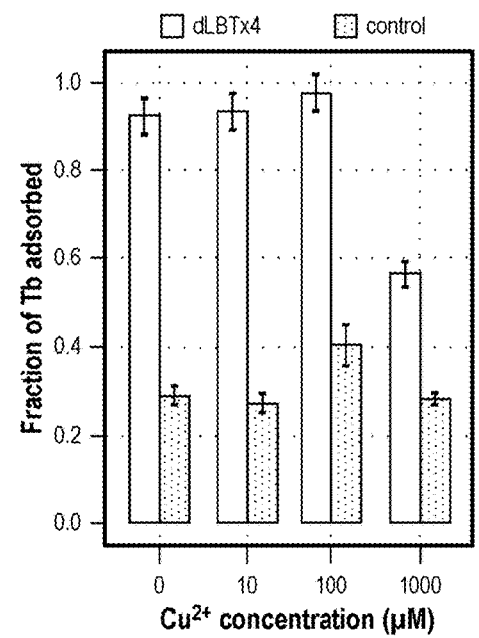
*FIG. 3A*     *FIG. 3B*
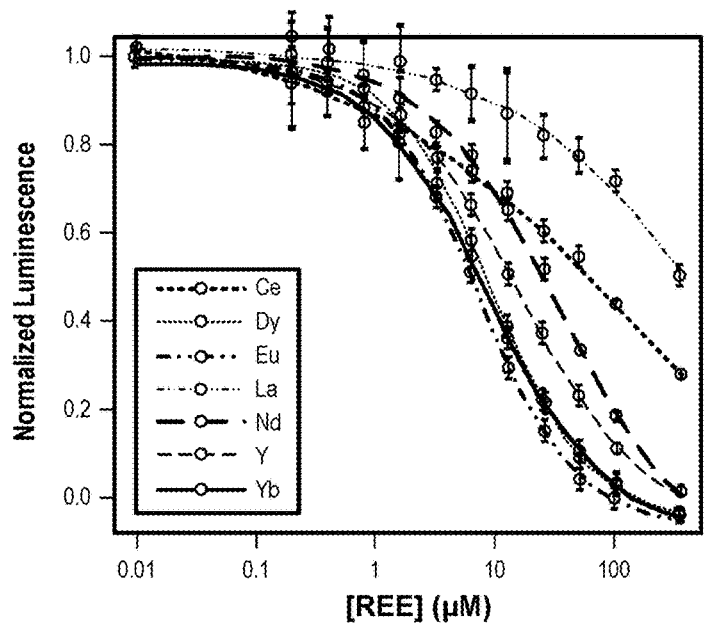 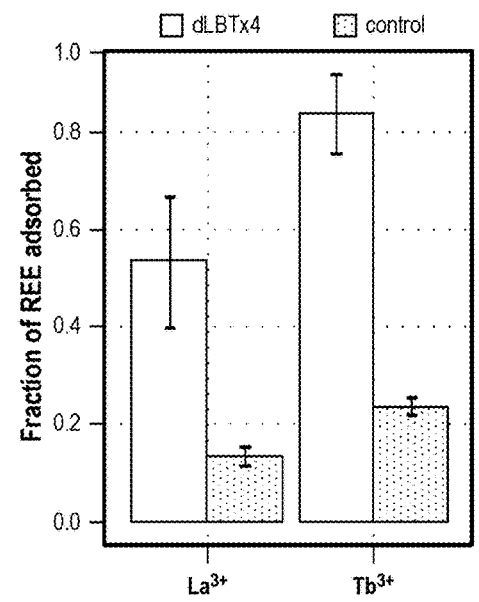
*FIG. 3C*     *FIG. 3D*

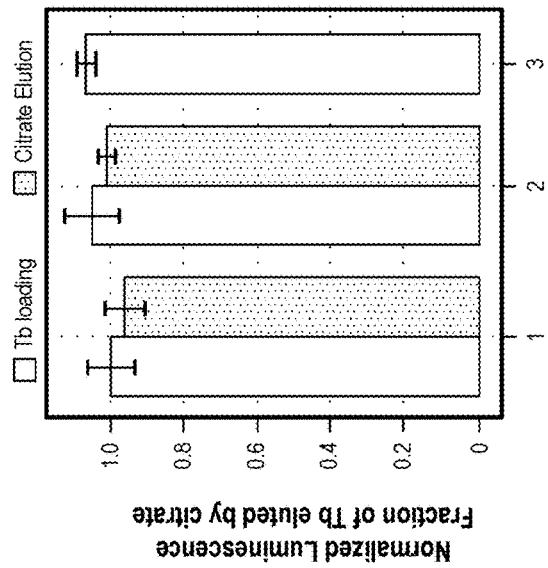
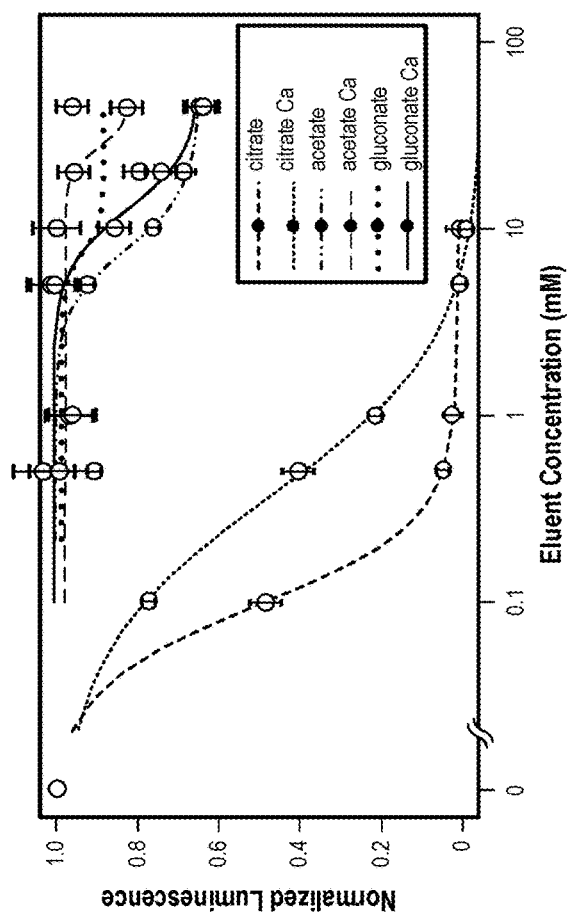
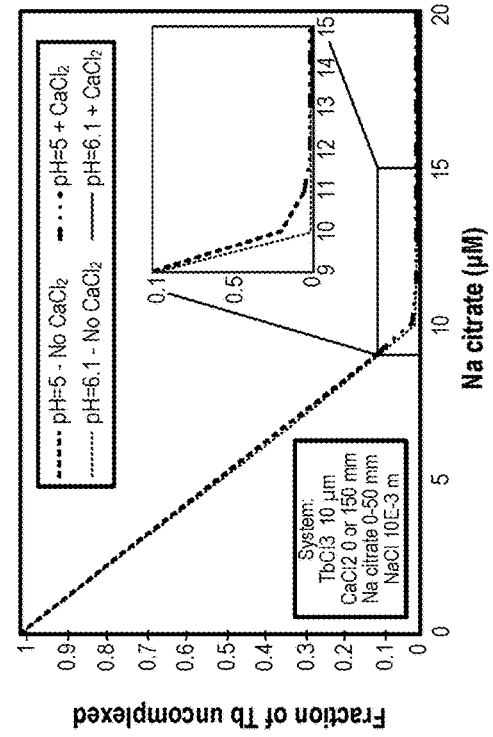
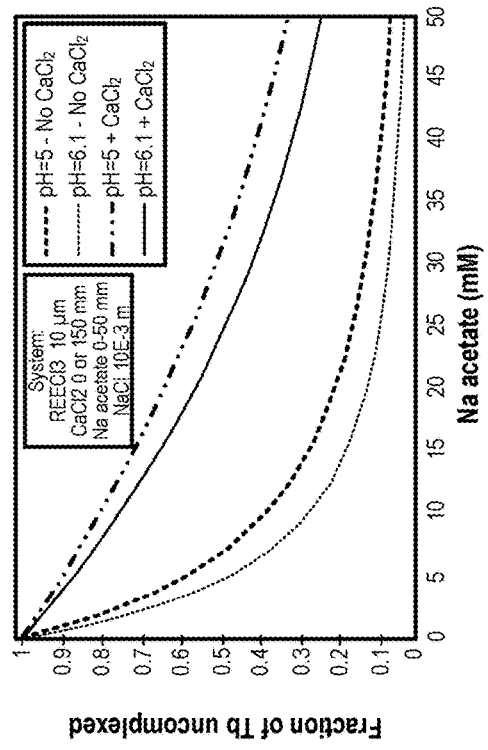
FIG. 4A
FIG. 4B
FIG. 4C
FIG. 4D

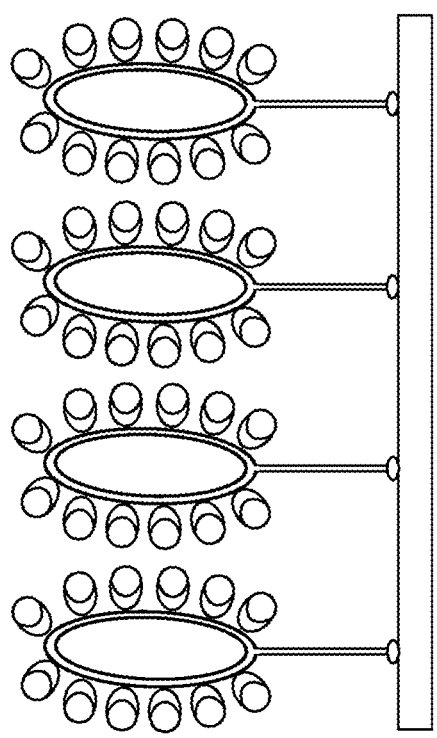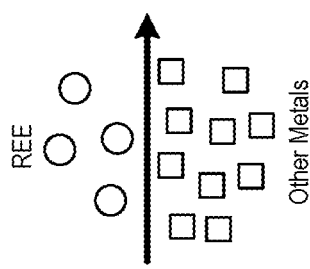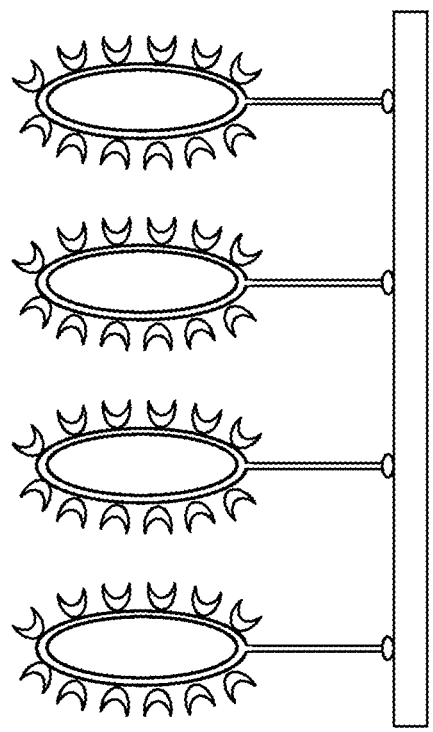
FIG. 12

ENGINEERED MICROBES FOR RARE EARTH ELEMENT ADSORPTION

CROSS-REFERENCE TO RELATED APPLICATION

This application is a continuation of U.S. patent application Ser. No. 15/400,948 filed on Jan. 6, 2017, and issued as U.S. Pat. No. 10,196,708, which is hereby incorporated by reference in its entirety.

STATEMENT REGARDING FEDERALLY SPONSORED RESEARCH

The United States Government has rights in this application pursuant to Contract No. DE-AC52-07NA27344 between the United States Department of Energy and Lawrence Livermore National Security, LLC for the operation of Lawrence Livermore National Laboratory.

STATEMENT REGARDING SEQUENCE LISTING

This application contains a Sequence Listing submitted in ASCII format via EFS-Web, and is hereby incorporated by reference in its entirety. The ASCII text file was created on Mar. 16, 2017, named 0775188076US00.txt, and is 5,632 bytes in size.

BACKGROUND

Rare earth elements ("REEs") are mined from the Earth's crust. Because of their unique physical and chemical properties, these elements are crucial in a growing number of high-tech products, including high-performance magnets, lasers, computer memory, cell phones, catalytic converters, camera and telescope lenses, and green technologies such as wind turbines and hybrid vehicles, to name a few.

Many countries, including the United States produce REEs, but China has been the dominate producer of REEs, accounting for between 70-90% of the supply of the world's REEs. REEs are difficult to mine in part because it is unusual to find them in concentrations high enough for economical extraction. Use of GPS-controlled drills and Gamma-ray sampling allows geologists to identify higher REE-containing ore. The ore is often laced with radioactive materials such as thorium and current methods for the extraction and processing of REEs requires large amounts of carcinogenic toxins including organic solvents, ammonia salts, and strong acids. Leaching of metals has high energy/capital costs, high $CO_2$ emissions, and many negative health and environmental impacts.

As the demand for REEs continues to surge at a rapid rate, there remains a need for tools to help increase and diversify the supply of REEs, develop clean and low cost extraction processes, improve efficiencies, and recapture REEs through reuse and recycling.

SUMMARY

Methods and materials are provided for the detection and/or extraction of REEs including, for example, genetically engineered microbes.

In some aspects, the disclosure provides genetically engineered microbes comprising an exogenous nucleic acid sequence encoding at least one rare earth element (REE) binding ligand.

In some aspects, the disclosure provides compositions comprising an amount of the genetically engineered microbes according to any embodiments described herein.

In some aspects, the disclosure provides systems comprising an amount of the genetically engineered microbes compositions microbes according to any embodiments described herein.

The disclosure also provides methods for extracting rare earth elements (REE) from a material comprising the steps of: (a) providing genetically engineered microbes comprising an exogenous nucleic acid sequence encoding at least one REE binding ligand; (b) contacting the genetically engineered microbes with a REE containing material, whereupon the REE binding ligand specifically binds at least a portion of the REE to form a microbe-REE complex; and (c) separating the microbe-REE complex from at least a portion of the material.

The disclosure also provides methods for detecting REE in a material comprising the steps of: (a) contacting genetically engineered microbes having an exogenous nucleic acid sequence encoding at least one REE binding ligand with the material; and (b) determining the amount of REE in at least a portion of the material.

In some embodiments, the microbe is a bacterium or bacteriophage.

In some embodiments, the bacterium is a Grain-negative bacterium. In other embodiments, the bacterium is a Gram-positive bacterium.

In some embodiments, the bacterium is selected from the group consisting of *Caulobacter crescentus* (*C. crescentus*), *Escherichia coli* (*E. coli*), *Bacillus*, and *Lactobacillus*.

In some embodiments, the REE binding ligand is expressed on the cell surface and/or within a cell surface protein. In some embodiments, the REE binding ligand is displayed on the cell surface by a surface layer (S-layer) protein, for example, RsaA from *C. crescentus*.

In some embodiments, the REE binding ligand is attached to the cell surface by a linker peptide, for example, a mucin protein.

In some embodiments, the REE binding ligand is a lanthanide binding tag (LBT). In some embodiments, the LBT comprises two lanthanide binding motifs that form a double-LBT (dLBT). In some embodiments, the LBT or double-LBT on the cell surface protein comprise a copy number selected from the group consisting of 1 copy, 2 copies, 4 copies, 8 copies, and 16 copies.

In some embodiments, the microbe further comprises at least one purification tag, for example, chitin binding protein (CBP), maltose binding protein (MBP), glutathione-S-transferase (GST), and poly(His).

In some embodiments, the binding affinity ($K_d$) of the REE binding ligand of the microbe to a REE is between about 1 µM and 200 µM.

In some embodiments, the REE binding ligand binds a REE selected from the group consisting of lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), scandium (Sc) and yttrium (Y).

In some embodiments, the genetically engineered microbes are viable, non-viable, or any combination thereof.

In some embodiments, the compositions described herein further comprise an amount of medium.

In some embodiments, the medium is supplemented with calcium ($Ca^{2+}$).

In some embodiments, the genetically engineered microbes are attached to a solid support.

In some embodiments, the solid support comprises a column, a membrane, or a bead.

In some embodiments, the solid support comprises alginate, acrylamide, regenerated cellulose, cellulose ester, or glass.

In some embodiments, the material is an aqueous medium. In some embodiments, the material is rare earth ores, geothermal brines, coal, coal byproducts, mine tailings, phosphogypsum, acid or salt leachate of solid materials, or other ore materials.

In some embodiments, the genetically engineered microbes are attached to a surface of a solid support.

In some embodiments, the REE containing material is refined to remove at least a portion of non-REE metals. In some embodiments, at least a portion of the non-REE metals are extracted using microbes.

In some embodiments, at least one step comprises addition of calcium.

In some embodiments, the binding of REE to the genetically engineered microbes is reversible.

In some embodiments, the methods described herein further comprise separating the REE from the genetically engineered microbes to produce regenerated genetically engineered microbes. In some embodiments, the separating is performed by acid-stripping. In other embodiments, the separating is performed using an amount of citrate.

In some embodiments, the methods described herein further comprise reusing the regenerated genetically engineered microbes.

In some embodiments, the material is known to contain an amount of REE. In other embodiments, the material is suspected to contain an amount of REE.

In some embodiments, the determining step is performed by inductively coupled plasma mass spectrometry (ICP-MS), thermogravimetry and differential scanning calorimetry (TGA-DSC), X-ray diffraction, or any combination thereof.

BRIEF DESCRIPTION OF THE DRAWINGS

FIGS. 2A-2F demonstrate adsorption of the rare earth element $Tb^{3+}$ to LBT-displayed cells. (FIG. 2A) Tb3+ titration of dLBT constructs with no added $Ca^{2+}$, measured by luminescence (ex/em 280/544). ICP-MS quantitation of $Tb^{3+}$ adsorption by dLBTx4 and control cells at increasing Tb3+ concentration in the absence (FIG. 2B) or presence (FIG. 2C) of 100 mM $Ca^{2+}$. The adsorption contribution of LBT in dLBTx4 was approximated by subtracting the total adsorbed $Tb^{3+}$ by the control strain from that adsorbed by dLBTx4, yielding 12.9±4.6 $Tb^{3+}$. The uncertainty in this expression was determined using error propagation. (FIG. 2D) $Tb^{3+}$ titration of dLBT constructs with 100 mM $Ca^{2+}$. The data from (FIG. 2A) were plotted as dotted lines for comparison. (FIG. 2E) ICP-MS quantitation of $Tb^{3+}$ (10 µM added) adsorption by dLBTx4 and control cells at different $Ca^{2+}$ concentrations. (FIG. 2F) ICP-MS quantitation of $Tb^{3+}$ (10 µM added) adsorption by dLBTx4 and control cells within the pH range of 4-6 in the presence of 100 mM $Ca^{2+}$.

FIGS. 3A-3D demonstrate REE adsorption specificity. (FIG. 3A) Competition binding experiments with dLBTx4 cells preloaded with 10 µM $Tb^{3+}$ followed by addition of various metal ions at concentrations up to 10 mM. (FIG. 3B) $Tb^{3+}$ adsorption to dLBTx4 and control cells at increasing $Cu^{2+}$ concentrations. The fraction of $Tb^{3+}$ adsorbed was determined by quantifying the soluble $Tb^{3+}$ concentrations before and after incubation with cells using ICP-MS. (FIG. 3C) Competition experiments with dLBTx4 cells preloaded with 10 µM $Tb^{3+}$ followed by addition of REE ions up to 352 µM. (FIG. 3D) $Tb^{3+}$ and $La^{3+}$ (20 µM each) adsorption to dLBTx4 and control cells. The fraction of REE absorbed was determined by ICP-MS. All experiments were performed in the presence of 150 mM $Ca^{2+}$. Error bars represent standard deviations of three replicates.

FIGS. 4A-4D show citrate-mediated REE desorption. (FIG. 4A) REE desorption and recovery were performed by preloading dLBTx4 cells with 10 µM $Tb^{3+}$ in the presence or absence of 150 mM $Ca^{2+}$ followed by the addition of increasing concentrations of citrate, gluconate or acetate. (FIG. 4B) Three cycles of $Tb^{3+}$ adsorption and desorption were performed with citrate (5 mM) in the presence of 150 mM $Ca^{2+}$. Bars depict the normalized luminescence signal for $Tb^{3+}$ loading and the fraction of $Tb^{3+}$ eluted using 5 mM citrate during each cycle as quantified by ICP-MS. (FIG. 4C, FIG. 4D) The predicted fraction of $Tb^{3+}$ that was not complexed with acetate or citrate, respectively, using the thermodynamic model. Results are shown for pH 5 and 6.1 within the range of acetate and citrate concentrations used in (FIG. 4A). Note that the concentration scale in FIG. 4D is expanded to focus on the rapid decline in uncomplexed Tb at low citrate concentrations. The individual $Tb^{3+}$ species present in the aqueous solution in the presence of acetate or citrate are shown in FIG. 9A and FIG. 9B, respectively.

(FIG. 10A) Fraction of metals adsorbed to engineered and control *E. coli* cells (DMP489), calculated by dividing the amount of metal adsorbed on the cell surface (calculated by subtracting the metal concentration remaining in solution after adsorption from the initial concentration in the leachate) from the initial concentration in the leachate. (FIG. 10B) One twentieth volume (relative to the initial leachate volume) of 5 mM citrate solution (pH 6) was used to recover REE adsorbed to *E. coli* LBT and control cells. The fold enrichment was calculated by dividing the metal concentration in the eluent from the initial concentration in the leachate. Metal concentrations were determined using ICP-MS.

FIG. 12 is a schematic of a biofilm containing genetically modified *Caulobacter* according to one embodiment of the present disclosure and formed on a supporting surface that is able to sequester REEs from solution. The genetically modified REE-adsorbing *Caulobacter* not only selectively sequesters dissolved REEs but also form a monolayer biofilm through their distinctive holdfasts, enabling a single step for REE extraction.

DETAILED DESCRIPTION

Figure 1A:
FIG. 1A shows a schematic diagram of engineered S-layer gene (rsaA) constructs with dLBT insertions. A muc1B spacer, encoding the human mucin protein, was appended to the C-terminal end of dLBT. The copy number of the resulting dLBT-mucR1 peptide was increased exponentially. The number labels of the constructs correspond to the lanes described in FIG. 1B.

The present disclosure relates to genetically engineered microbes for detecting and/or extracting rare earth elements (REE) from REE-containing materials.

After reading this description it will become apparent to one skilled in the art how to implement the invention in various alternative embodiments and alternative applications. However, all the various embodiments of the present invention will not be described herein. It will be understood that the embodiments presented here are presented by way of example only, and not limitation. As such, this detailed description of various alternative embodiments should not be construed to limit the scope or breadth of the present invention as set forth below.

The detailed description is divided into various sections only for the reader's convenience and disclosure found in any section may be combined with that in another section. Titles or subtitles may be used in the specification for the convenience of a reader, which are not intended to influence the scope of the present disclosure.

The practice of the present disclosure will employ, unless otherwise indicated, conventional techniques of bacterial culture, molecular biology, cell biology and recombinant DNA, which are within the skill of the art. See, e.g., Sambrook and Russell eds. (2001) Molecular Cloning: A Laboratory Manual, 3$^{rd}$ edition; the series Ausubel et al. eds. (2007) Current Protocols in Molecular Biology; the series Methods in Enzymology (Academic Press, Inc., N.Y.); McPherson et al. (1991) PCR 1: A Practical Approach (IRL Press at Oxford University Press); McPherson et al. (1995) PCR 2: A Practical Approach; Harlow and Lane eds. (1999) Antibodies, A Laboratory Manual; Freshney (2005) Culture of Animal Cells: A Manual of Basic Technique, 5$^{th}$ edition; Gait ed. (1984) Oligonucleotide Synthesis; U.S. Pat. No. 4,683,195; flames and Higgins eds. (1984) Nucleic Acid Hybridization; Anderson (1999) Nucleic Acid Hybridization; Hames and Higgins eds. (1984) Transcription and Translation; IRL Press (1986) Immobilized Cells and Enzymes; Perbal (1984) A Practical Guide to Molecular Cloning; Miller and Calos eds. (1987) Gene Transfer Vectors for Mammalian Cells (Cold Spring Harbor Laboratory); Makrides ed. (2003) Gene Transfer and Expression in Mammalian Cells; Mayer and. Walker eds. (1987) Immunochemical Methods in Cell and Molecular Biology (Academic Press, London); Herzenberg et al. eds (1996) Weir's Handbook of Experimental Immunology; Manipulating the Mouse Embryo: A Laboratory Manual, 3$^{rd}$ edition (2002) Cold Spring Harbor Laboratory Press; Sohail (2004) Gene Silencing by RNA Interference: Technology and Application (CRC Press).

Unless the context indicates otherwise, it is specifically intended that the various features of the invention described herein can be used in any combination. Moreover, the disclosure also contemplates that in some embodiments any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

All numerical designations, e.g., pH, temperature, time, concentration, and molecular weight, including ranges, are approximations which are varied (+) or (−) by increments of 1.0 or 0.1, as appropriate, or alternatively by a variation of +1-15%, or alternatively 10%, or alternatively 5%, or alternatively 2%. It is to be understood, although not always explicitly stated, that all numerical designations are preceded by the term "about." It is to be understood that such range format is used for convenience and brevity and should be understood flexibly to include numerical values explicitly specified as limits of a range, but also to include all individual numerical values or sub-ranges encompassed within that range as if each numerical value and sub-range is explicitly specified. For example, a ratio in the range of about 1 to about 200 should be understood to include the explicitly recited limits of about 1 and about 200, but also to include individual ratios such as about 2, about 3, and about 4, and sub-ranges such as about 10 to about 50, about 20 to about 100, and so forth. It also is to be understood, although not always explicitly stated, that the reagents described herein are merely exemplary and that equivalents of such are known in the art.

It must be noted that as used herein and in the appended claims, the singular forms "a," "an," and "the" include plural referents unless the context clearly dictates otherwise. Thus, for example, reference to "a microbe" includes a plurality of microbes.

Definitions

As used herein the following terms have the following meanings:

The term "about," as used herein when referring to a measurable value such as an amount or concentration and the like, is meant to encompass variations of 20%, 10%, 5%, 1%, 0.5%, or even 0.1% of the specified amount.

The terms or "acceptable," "effective," or "sufficient" when used to describe the selection of any components, ranges, dose forms, etc. disclosed herein intend that said component, range, dose form, etc. is suitable for the disclosed purpose.

Also as used herein, "and/or" refers to and encompasses any and all possible combinations of one or more of the associated listed items, as well as the lack of combinations when interpreted in the alternative ("or").

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

Microbes

Aspects of the disclosure provide microbes genetically engineered to express REE binding ligands. Suitable microbes include, for example, bacteria (e.g., *Caulobacter* and *Escherichia*), yeast (e.g., *Saccharomyces* and *Candida*), bacteriophage, and algae. In some embodiments, the microbe is a bacterium, for example a Gram-positive or a Gram-negative bacterium. In some embodiments the microbe is a bacteriophage.

Non-limiting examples of suitable bacteria include *Acetobacter* spp., Acidithiobacillus spp., *Acinetobacter* spp., *Aeromonas* spp., *Agrobacterium* spp., *Alcaligenes* spp., *Archaebacteria* spp., *Aquaspirrilum* spp., *Arthrobacter* spp., *Azotobacter* spp., *Bacillus* spp., *Caulobacter* spp., *Chlamydia* spp., *Chromatium* spp., *Chromobacterium* spp., *Citrobacter* spp., *Clostridium* spp., *Comamonas* spp., *Corynebacterium*. spp., *Cyanobacteria* spp., *Escherichia* spp., *Flavobacterium* spp., *Geobacillus* spp., *Geobacter* spp., *Gluconobacter* spp., *Lactobacillus* spp., *Lactococcus* spp., *Microlunatus* spp., *Mycobacterium* spp., *Pantoea* spp., *Pseudomonas* spp., *Ralstonia* spp., *Rhizobium* spp., *Rhodococcus* spp., *Saccharopolyspora* spp., *Salmonella* spp., *Serratia* spp,. *Sinorhizobium* spp., *Stenotrophomonas* spp., *Streptococcus* spp., *Streptomyces* spp., *Synechocystis* spp., *Thermus* spp., *Xanthomonas* spp., and *Zymonas* spp.

In one embodiment the bacterium is selected from the group consisting of *Caulobacter* (e.g., *C. crescentus, C. bacteroides, C. daechungensis, C. fusifbrmis, C. ginsengisoli, C. halobacteroides, C. henricii, C. intermedius, C. leidyi, C. maxis, C. mirabilis, C. profundus, C. segnis, C. subvibrioides, C. variabilis,* and *C. vibrioides*), *Escherichia* (e.g., *E. albertii, E. coli, E. fergusonii, E. hermannii,* and *E. vulneris*), *Bacillus* (e.g., *B. licheniformis, B. cereus* and *B. subtilis*), and *Lactobacillus* (e.g., *L. Lactis, L. Acidophilus, L. Brevis, L. Bulgaricus, L Casei, L Helveticus, L. reuteri, L. rhamnosus, L. Rhamnosus* GG, *L. rhamnosus* CR-1, *L. plantarum,* and *L.* Silivarius). In one preferred embodiment, the bacterium is *C. crescentus. Caulobacter* are particularly suitable because they are considered to be non-pathogenic, heavy metal resistant and oligotrophic. In another preferred embodiment, the bacterium is *E. coli.*

Non-limiting examples of suitable bacteriophage include T7 bacteriophage, M13 bacteriophage, Mu bacteriophage, T5 bacteriophage, T3 bacteriophage, bacteriophage Qβ, and MS2 bacteriophage. In some embodiment, the bacteriophage is lysogenic. In other embodiments, the bacteriophage is lytic.

In one embodiment, the REE binding ligand is expressed by the cell, for example, on the cell surface through anchoring to the S-layer protein and/or an outer membrane protein. The heterologous REE binding ligand can be expressed as a fusion product with the cell surface protein of the bacterium. Many bacteria assemble layers composed of repetitive, regularly aligned, proteinaceous subunits on the outer surface of the cell. Such layers are commonly known as S-layers and are found on members of every taxonomic group of walled bacteria including: *Acinetobacter* spp., *Aquaspirrillum* spp., *Archaebacteria* spp., *Bacillus* spp., *Caulobacter* spp., *Chlanydia* spp., *Chromatium* spp., *Clostridium* spp., *Cyanobacteria* spp., and *Lactobacillus* spp. S-layer-containing bacteria are particularly suitable for the uses described herein because the S-layer can serve as a metal-binding peptide anchor. Suitable S-layer proteins include, for example, OlpA, SbsA, SbsB, SbsC, RsaA, SlpA, CbsA, SlpH1, and SlpH2. In one embodiment, the S-layer protein is RsaA. Suitable outer membrane proteins include, for example, OmpA, Lpp-ompA, OmpX, phospholipase A, porins (e.g., OmpF, PhoE, LamB, and ScrY), and TonB-dependent iron siderophore transporters (e.g., FhuA and FepA).

In some embodiments, the REE binding ligand is coupled with (e.g., attached or joined to) the cell surface by a linker peptide. In some embodiments, multiple copies of the REE binding ligand are coupled with (e.g., attached or joined to) the cell surface by a linker peptide. Multiple copies of the REE binding ligand can be inserted into the same insertion site of the anchor protein (e.g., S-layer protein). Selection of an appropriate linker sequence is important, as it can affect the function and physical properties of the resulting fusion protein. The linkers can be used to control the distance and the orientation of the binding ligand. In some embodiments, flexible and hydrophilic linkers are chosen so as to not overly constrain and thereby disturb the functions of the REE binding ligands. In other embodiments, the peptide linkers are rigid linkers. In yet other embodiments, the linkers are cleavable linkers. In some embodiments, the linker peptide is a mucin protein. Mucin proteins and mucin-domains of proteins contain a high degree of glycosylation which structurally allows mucin proteins and other polypeptides comprising mucin domains to behave as stiffened random coils. Mucin domains linker peptides may comprise tandem amino acid repeat units that may vary in length from about 8 amino acids to 150 amino acids per each tandem repeat unit. The number of tandem repeat units may vary between 1 and 5 in a mucin-domain linker peptide. In some embodiments, each of the REE binding ligands can be separated by a peptide linker (i.e., spacer), for example, muc1B. In some embodiments, the peptide linker is appended to the C-terminal end, the N-terminal end, or both ends of the REE binding ligand.

In some embodiments, bacteria are genetically modified to have altered lipopolysaccharides (LPS). LPS, also known as endotoxin, is the major constituent of the outer leaflet of the outer membrane of virtually all Gram-negative bacteria. It is contemplated that altering the LPS functionalizes surface bound phosphates with non-charged functional groups, decreases the non-specific metal binding to the native bacterial cell wall, and improve on the REE purity of the products upon desorption. An example of a suitable LPS-altered bacterium is the *E. coli* lpxT mutant and pmrA constitutive strain. Herrera C M et al., (2010) *Mol Microbiol.* 76:1444-1460. In some embodiments, bacteria with genetically modified LPS reduce background absorption of particular elements (e.g., iron, lead, and uranium) and increase REE purity upon desorption.

REE Binding Ligands

Aspects of the present disclosure provide genetically engineered microbes expressing REE binding ligands, for example, lanthanide binding tags (LBT). LBTs are short peptide sequences of up to 20 amino acids that are optimized to selectively bind trivalent lanthanide ($Ln^{3+}$) ions. As LBTs are built from encoded amino acids they can be introduced as co-expression tags at the DNA level to create fusion proteins.

In some embodiments, the LBTs comprise two lanthanide binding motifs that form a double LBT (dLBT). Martin, L. J. et al., *J. Am. Chem. Soc.* 2007, 129 (22) 7106-7113. In other embodiments, the LBT comprises one lanthanide binding motifs that form a single LBT. The single or dLBTs can be expressed in single copy or multiple copy numbers, for example, 2 copies, 3 copies, 4 copies, 5 copies, 6 copies, 7 copies, 8 copies, 9 copies, 10 copies, 11 copies, 12 copies, 13 copies, 14 copies, 15 copies, 16 copies, 17 copies, 18 copies, 19 copies, 20 copies, 21 copies, 22 copies, 23 copies, 24 copies, 25 copies, 26 copies, 27 copies, 28 copies, 29 copies, 30 copies, 31 copies, 32 copies, 33 copies, 34 copies, 35 copies, 36 copies, 37 copies, 38 copies, 39 copies, 40 copies, 41 copies, 42 copies, 43 copies, 44 copies, 45 copies, 46 copies, 47 copies, 48 copies, 49 copies, 50 copies, or more copies. In some embodiments, the dLBTs can be expressed as 2 copies, 4 copies, 8 copies, 16 copies, 32 copies, 64 copies, 128 copies, or more copies. In some embodiments, the dLBTs can be expressed as about 50 copies, about 56 copies, about 60 copies, about 66 copies, about 70 copies, about 76 copies, about 80 copies, about 86 copies, about 90 copies, about 96 copies, about 100 copies, about 110 copies, about 120 copies, about 130 copies, about 140 copies, about 150 copies, about 160 copies, about 170 copies, about 180 copies, about 190 copies, about 200 copies, or more copies. In some embodiments, the single LBT or dLBT is expressed on the cell surface protein as a single copy (e.g., dLBTx1), 2 copies (e.g., dLBTx2), 4 copies (e.g., dLBTx4), 8 copies (e.g., dLBTx8), or 16 copies (e.g., dLBTx16). For example, constructs encoding the S-layer protein RsaA can be generated to contain dLBTx8. In some embodiments, each of the copies can be separated by a peptide linker (i.e., spacer), for example, muc1B. In some embodiments, the peptide linker is appended to the C-terminal end, the N-terminal end, or both ends of the LBT or dLBT.

The LBTs can be inserted into any permissible insertion site. In some embodiments, LBTs can be inserted into the S-layer protein RsaA at an amino acid position selected from the group consisting of 574, 622, 690, 723, and 944. Nomellini et al., *Appl. Environ. Microhiol.* 2007, 73 (10) 3245-3253. In some embodiments, LBTs can be inserted into the S-layer protein RsaA at amino acid position 723. In other embodiments, LBTs can be inserted at the C-terminal end of OmpA.

REE are a group of seventeen chemical elements that includes yttrium and fifteen lanthanide elements. Scandium is found in most REE deposits and is often included.

TABLE 1

Rare Earth Elements

| Name | Symbol | Atomic Number | Name | Symbol | Atomic Number |
| --- | --- | --- | --- | --- | --- |
| lanthanum | La | 57 | dysprosium | Dy | 66 |
| cerium | Ce | 58 | holmium | Ho | 67 |
| praseodymium | Pr | 59 | erbium | Er | 68 |
| neodymium | Nd | 60 | thulium | Tm | 69 |
| promethium | Pm | 61 | ytterbium | Yb | 70 |
| samarium | Sm | 62 | lutetium | Lu | 71 |
| europium | Eu | 63 | scandium | Sc | 21 |
| gadolinium | Gd | 64 | yttrium | Y | 39 |
| terbium | Tb | 65 | | | |

The REE binding ligands can bind any of lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), scandium (Sc), yttrium (Y), or any combination thereof.

In some embodiments, the genetically engineered microbes further comprise at least one purification tag. A purification tag is a sequence of amino acids that can be attached to a protein (e.g., a fusion protein) to permit purification of the protein (and microbe expressing said protein) from the extracellular medium. Non-limiting examples of suitable purification tags include chitin binding protein (CBP), maltose binding protein (MBP), glutathione-S-transferase (GST), poly(His), thioredoxin A (TrxA), small ubiquitin related modifier (SUMO), ketosteroid isomerase (KSI), and TrpΔLE.

In some embodiments, the REE binding ligand (e.g., LBT) binds a lanthanide ion (e.g. a REE) with a binding affinity ($K_d$) of between about 1 nM and 500 μM, about 100 nM and 200 μM, or about 500 nM and 1 μM. In some embodiments, the $K_d$ is between about 500 nM and about 200 μM, about 1 μM and 200 μM, or about 50 μM and 100 μM. In some embodiments, the $K_d$ is about 1 μM, about 5 μM, about 10 μM, about 15 μM, about 30 μM, about 40 μM, about 50 μM, about 60 μM, about 70 μM, about 80 μM, about 90 μM, about 100 μM, about 110 μM, about 120 μM, about 130 μM, about 140 μM, about 150 μM, about 160 μM, about 170 μM, about 180 μM, about 190 μM, about 200 μM, or more. In some embodiments, the $K_d$ is in the μM range. In other embodiments, the $K_d$ is in the nM range. In still other embodiments, the $K_d$ is in the pM range. Affinity can be determined by any suitable means known to one of skill in the art. Non-limiting examples include, titration with REE and detection using fluorescence, circular dichroism, NMR or calorimetry. In the case of tightly binding sequences, it may be necessary to employ competition experiments.

The microbes of the present disclosure can be genetically modified by any suitable methodology. As a non-limiting example, one or more of the nucleic acids (e.g., nucleic acid encoding for the lanthanide binding tag (LBT)) associated with the disclosure can be expressed in a recombinant expression vector. As used herein, a "vector" may be any of a number of nucleic acids into which a desired sequence or sequences may be inserted, such as by restriction and ligation, for transport between different genetic environments or for expression in a host cell. Vectors are typically composed of DNA, although RNA vectors are also available. Vectors include, but are not limited to: plasmids, fosmids, phagemids, virus genomes and artificial chromosomes.

A cloning vector is one which is able to replicate autonomously or integrated in the genome in a host cell, and which can be further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host cell. In the case of phage, replication may occur actively during a lytic phase or passively during a lysogenic phase.

An expression vector is one into which a desired nucleic acid sequence may be inserted, for example by restriction and ligation, such that it is operably joined to regulatory sequences and may be expressed as an RNA transcript. Vectors may further contain one or more marker sequences suitable for use in the identification of cells that have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, luciferase or alkaline phosphatase), and genes which visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined. When the nucleic acid molecule that encodes any of the genes associated with the claimed invention is expressed in a cell, a variety of transcription control sequences (e.g., promoter/enhancer sequences) can be used to direct its expression. The promoter can be a native promoter, i.e., the promoter of the gene in its endogenous context, which provides normal regulation of expression of the gene. In some embodiments the promoter can be constitutive, i.e., the promoter is unregulated allowing for continual transcription of its associated gene. In other embodiments, the promoter is an inducible promoter. A variety of conditional promoters also can be used, such as promoters controlled by the presence or absence of a molecule. Suitable promoters include, for example, T5, T7, rhamnose, arabinose (e.g., $P_{BAD}$), and PhoA.

Expression vectors containing all the necessary elements for expression are commercially available and known to those skilled in the art. See, e.g., Sambrook et al., Molecular Cloning: A Laboratory Manual, Fourth Edition, Cold Spring Harbor Laboratory Press, 2012. Cells are genetically engineered by the introduction into the cells of heterologous DNA (RNA). That heterologous DNA (RNA) is placed under operable control of transcriptional elements to permit the expression of the heterologous DNA in the host cell. A nucleic acid molecule that comprises a gene associated with the invention can be introduced into a cell or cells using methods and techniques that are standard in the art.

A nucleic acid, polypeptide or fragment thereof described herein can be synthetic. As used herein, the term "synthetic" means artificially prepared. A synthetic nucleic acid or polypeptide is a nucleic acid or polypeptide that is synthesized and is not a naturally produced nucleic acid or polypeptide molecule (e.g., not produced in an animal or organism). It will be understood that the sequence of a natural nucleic acid or polypeptide (e.g., an endogenous nucleic acid or polypeptide) may be identical to the sequence of a synthetic nucleic acid or polypeptide, but the latter will have been prepared using at least one synthetic step.

In some embodiments, a suitable dLBT nucleic acid comprises a nucleotide sequence having at least about 80%, at least about 85%, at least about 90%, at least about 95%, at least about 99%, or 100% nucleotide sequence identity of SEQ ID NO. 1, SEQ ID NO. 2, SEQ ID NO. 3, SEQ ID NO. 4, or SEQ ID NO. 6. In some embodiments, a suitable dLBT polypeptide comprises an amino acid sequence encoding a polypeptide comprises a sequence having at least about 80%, at least about 85%, at least about 90%, at least about 95%, at least about 99%, or 100% amino acid sequence identity of SEQ ID NO. 5. In some embodiments, a suitable dLBT-muc1B nucleic acid comprises a nucleotide sequence having at least about 80%, at least about 85%, at least about 90%, at least about 95%, at least about 99%, or 100% nucleotide sequence identity of SEQ ID NO. 7, SEQ ID NO. 8, or SEQ ID NO. 9.

In one embodiment, the expression vector further comprises, or alternatively consists essentially of, or yet further consists of a suicide gene. Expression of the suicide gene may be regulated by the same or different promoter as that which expresses the REE binding ligand-encoding nucleotide. A suicide gene is one that allows for the negative selection of the cells. In the methods described herein, a suicide gene is used as a safety system, allowing the cells expressing the gene to be killed by introduction of a selective agent. A number of suicide gene systems have been identified, including the herpes simplex virus thymidine kinase (tk or TK) gene, the cytosine deaminase gene, the varicella-zoster virus thymidine kinase gene, the nitroreductase gene, the *E. coli* gpt gene, and the *E. coli* deo gene.

Compositions

The present disclosure also provides composition comprising an amount of the genetically engineered microbes disclosed and described herein. In some embodiments, the compositions further comprise an amount of medium comprising, for example, PYE or LB media as a base media. In other embodiments, the medium can comprise a minimal medium with sugar or yeast extract as additional supplements. The composition can comprise one or more additional substances that can be consumed by the genetically engineered microbe to keep the relevant microbe alive or stimulate its growth. Non-limiting examples of additional substances include mucopolysaccharides, oligosaccharides, polysaccharides, amino acids, vitamins, trace elements, nutrient precursors and proteins. In one embodiment, the additional substance is calcium salt. It is contemplated that the addition of calcium salt in the growth media facilitates, in part, more robust production and/or stability of S-layer protein.

In some embodiments the growth media composition comprises an agar plate or stab culture.

In some embodiments, the genetically engineered microbes are viable, non-viable, or any combination thereof during the REE biosorption step.

In some embodiments, the composition may include a cryoprotectant agent. Non-limiting examples of cryoprotectant agents include a glycol (e.g., ethylene glycol, propylene glycol, and glycerol), dimethyl sulfoxide (DMSO), formamide, sucrose, trehalose, dextrose, and any combinations thereof.

In some embodiments, the genetically engineered microbe compositions are freeze-dried. Any suitable method known by one of skill in the art can be used. Freeze dry buffers may be included. In other embodiments, the compositions are lyophilized. Lyophilization buffers may be included.

Biosorption Systems

Also provided are systems (i.e., biosorption/adsorption media) for REE extraction comprising an amount of the genetically engineered microbes according to the disclosure above. In addition, provided herein are cell-free systems for use in the same.

In some embodiments, the genetically engineered microbes are attached to a solid support, for example, a column, a membrane, a bead, or the like. The solid support can be any suitable composition known to one of skill in the art including, for example, a polymer, alginate, acrylamide, regenerated cellulose, cellulose ester, plastic, or glass.

These biosorption media, which include, for example, biofilm, microcapsule, and carbon nanotube embedded membranes can be used for adsorption under continuous flow. It is contemplated that microbe immobilization in biosorption media for use in flow through setups allows for complete (or substantially complete) separation of REEs from REE-containing mixed metal solutions in a single step and, for example, without the need of centrifugation, filtration, or both.

In one embodiment, the microbes are immobilized via the formation of a biofilm. A biofilm is a layer of microorganisms that are attached to a surface. For biofilm formation, microbes having the distinctive ability to self-immobilize on supported solid surfaces, for example, *Caulobacter* may be used. *Caulobacter* forms uniform, high-density biofilms owing to a strongly adhesive organelle, a holdfast that is present at the distal tip of the stalk. In some embodiments, the biofilms are monolayers. The biofilms can be housed within a bioreactor including, for example, a spiral-sheet bioreactor, a fiber brush bioreactor, or other supported vehicles suspended in the bioreactor. In other embodiments, the biofilms are three-dimensional. 3D mushroom-like structures are observed to form interspersed with monolayer biofilms. (Entcheva-Dimitrov P. et al., (2004) *J of Bacteriology* 186(24):8254-8266). These 3D structures can promote cell detachment, cause clogging and disruption of solution diffusion and transport, which are undesirable for REE adsorption. In some embodiments, to minimize 3D structures, a figH microbial mutant that cannot make a functional flagellum can be generated. (Entcheva-Dimitrov P. et al., (2004) *J of Bacteriology* 186(24):8254-8266). It is contemplated that knocking out the figH gene will eliminate mushroom-like structures, promote monolayer biofilm formation, and therefore enhance REE adsorption.

Microbes can be immobilized on any suitable supporting material for optimal microbe attachment (e.g., fast, stable) known to one of skill in the art. Non-limiting examples of supporting material include carbon film, glass, steel, Teflon, polyethylene and the like. Growth media, temperature, inoculum size, incubation temperature, or any combination thereof can be varied to determine the optimal conditions for biofilm formation on each supporting material. In some embodiments, holdfast-containing *Caulobacter* strains will facilitate biofilm formation.

In one embodiment, the genetically engineered microbes are bound (i.e., embedded) within or to the surface of a bead. In some embodiments, the bead is a polymer. Suitable polymers include PEG (e.g., ~10% PEG), alginate (e.g., ~2% calcium alginate), and acrylamide (e.g., ~10% polyacrylamide). In other embodiments the beads are glass, plastic, or steel.

In one embodiment, the microbes are immobilized through fabrication of microcapsules. The synthesis and fabrication of microcapsules in the 10 to 1000's microns size range for material encapsulation, storage and release have received significant attention in the past years for different applications, in order to isolate and protect the core materials from the surrounding environment. For example, encapsulation can protect enzymes from denaturing by solvents, shield probiotic bacteria from high temperature and digestive system, and protect chemicals from deteriorating due to oxidation and moisture with an inert matrix or shell. Moreover, encapsulations can allow and improve the controlled release of the encapsulated ingredient or immobilize living cells for controlled growth.

Any suitable microencapsulation techniques known to one of skill in the art can be used to encapsulate the microbes of the present disclosure. In some embodiments, polymers such as acrylamide, silicone, and acrylate are used. Polymers have become the primary shell/matrix material used in this area because of the high solubility in organic solvents, easy and versatile formation, crosslinkable nature, sufficient strength and wide variety of chemistries.

Figure 13:
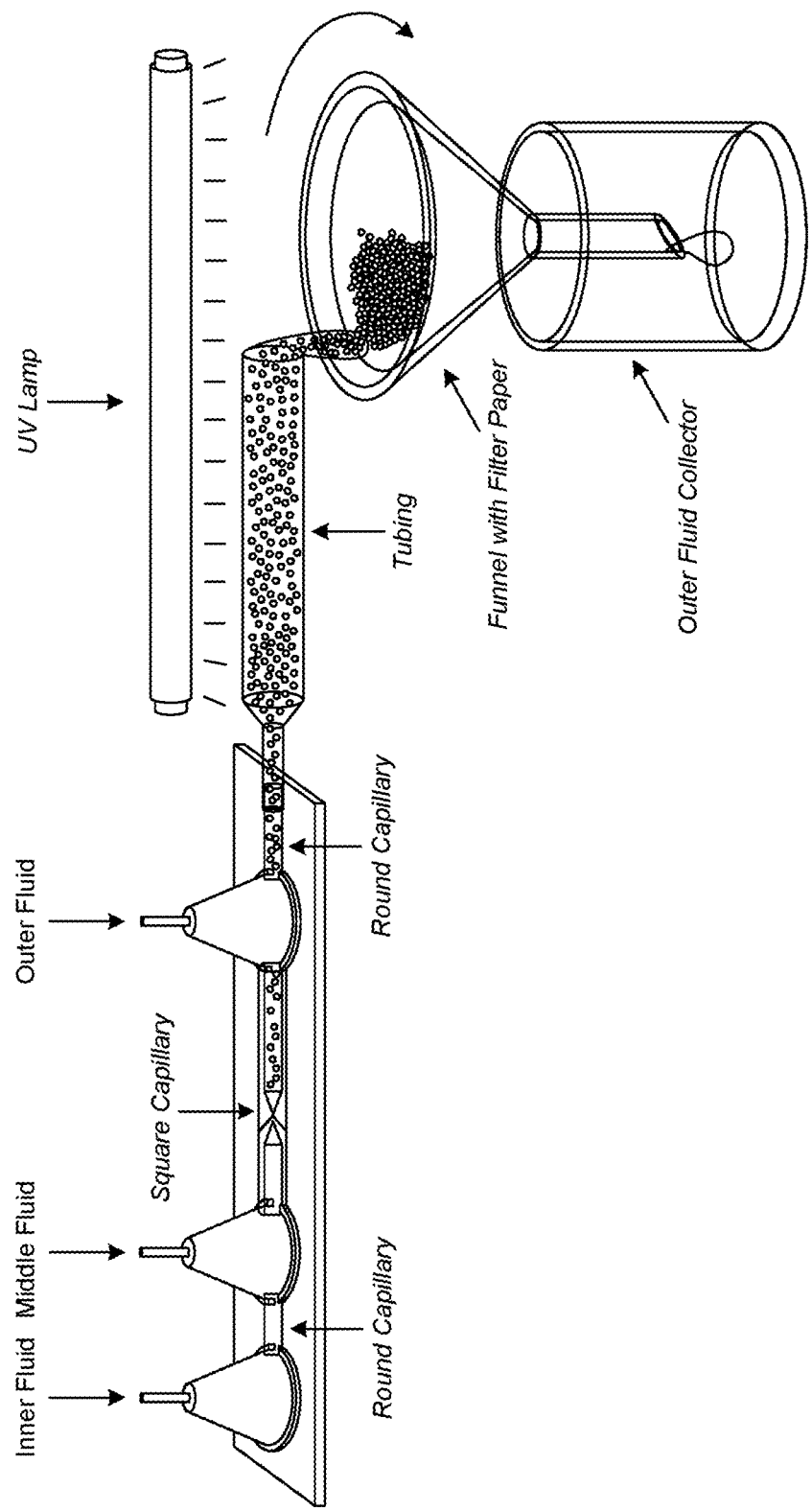
FIG. 13 is a schematic showing the microfluidic setup for emulsion generation. Three fluids (i.e., inner fluid, middle fluid, and outer fluid) were flown inside the device and emulsion drops were generated near the entrance of exit capillary. Drops were then exposed to (JV to crosslink into capsules/particles and then collected.
Figure 14:
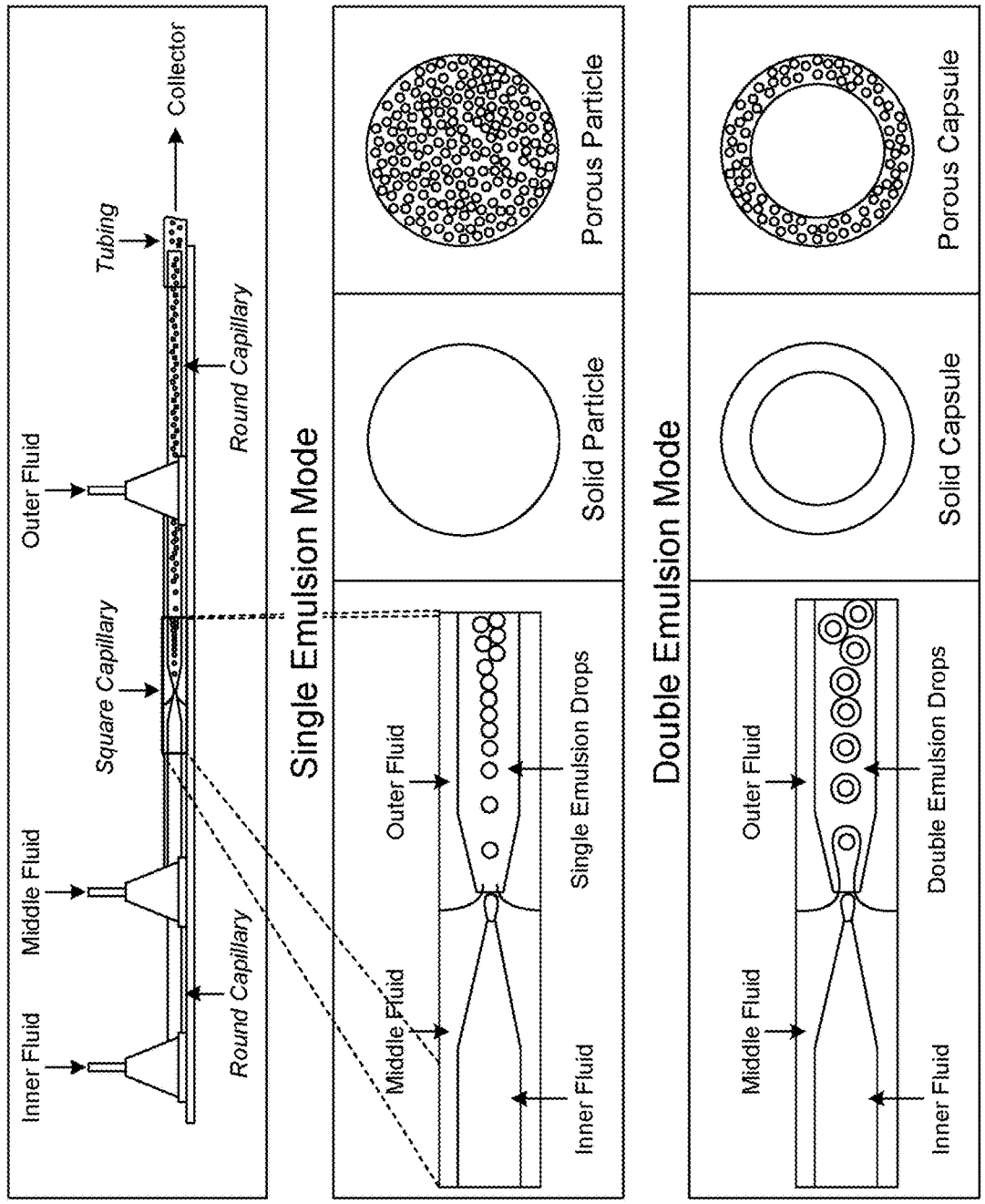
FIG. 14 is a schematic showing the single/double emulsion generation. In single emulsion mode, middle fluid and outer fluid are the same carrier solution. Inner fluid is the cell-containing polymer solution. In double emulsion mode, outer fluid is the carrier fluid and middle fluid is the polymer solution. Inner fluid is the aqueous cell-containing buffer solution. For both modes, different porosities in the microstructure can be introduced.

Microencapsulation techniques are known to one of skill in the art. In some embodiments, microfluidics are used to produce tailored particles and capsules. The majority of the microfluidic devices are built using poly(dimethylsiloxane) (PDMS). McDonald J. C., et al. (2002) *Acc Chem Res.* 35(7): 491499. Meanwhile, microfluidic devices based on glass microcapillaries was developed in order to overcome the limitation of usable solution and the difficulty of selective coating for more versatile capsule/particle generation. Utada A. S., et al., (2005) *Science* 308(5721):537-541; Ye C., et al. (2010) *J R Soc Interface* 7 Suppl 4:S461-473. Moreover, triple or quadruple emulsion systems can also be used to allow additional hierarchical layers in the drops for more complex applications. Abate A. R. et al. (2009) *Small* 5(18):2030-2032. Lastly, polymer particles and capsules can have a range of porosities through the microstructure. After polymers get crosslinked, the microcapsules and/or beads described above can be packed into extraction columns. An example of microfluidic setup for emulsion generation is depicted in FIG. 13. Device running in single and double emulsion modes are shown in FIG. 14, respectively.

Figures 15A, 15B, 15C:
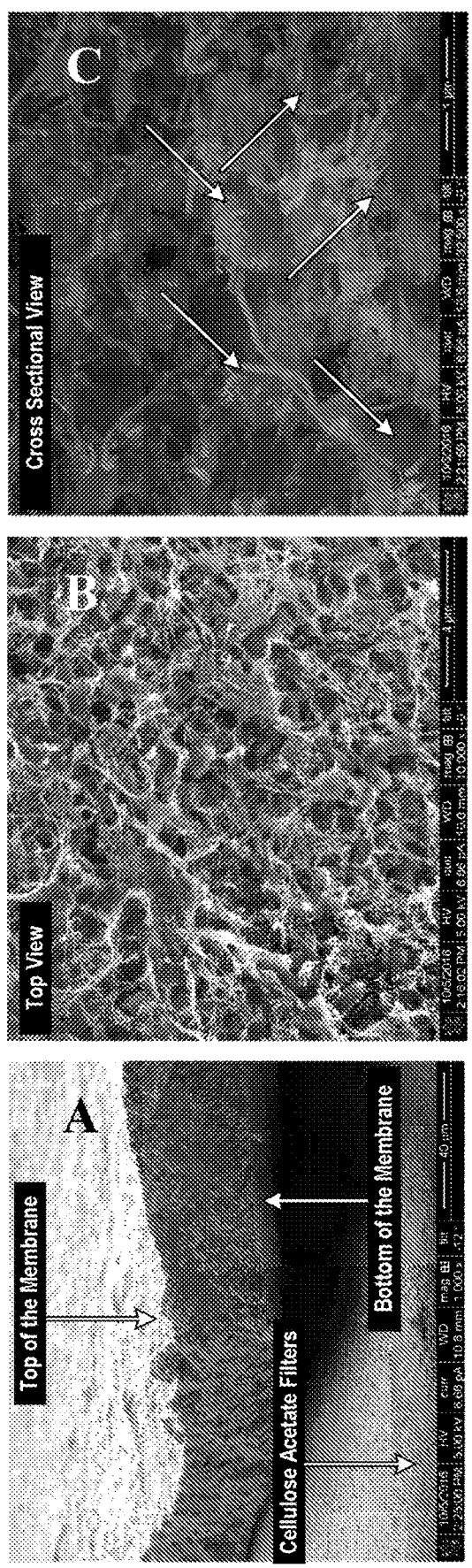
FIG. 15A is a scanning electron microscopy image (cross-section) of a cellulose acetate filter (0.2 μM) based CNT membrane. After fixation, the bacteria/CNT membrane detached from the cellulose acetate filter. The volume of the membrane is estimated to be about $3.64 \times 10^{10}$ μm$^3$.
FIG. 15B is a scanning electron microscopy image of a top view of the cellulose acetate filter based membrane. Bacteria are uniformly trapped in the CNT networks.
FIG. 15C is a cross-sectional view of the cellulose acetate filter based membrane of FIG. 13B. Arrows point to entrapped bacteria.

In another embodiment, the microbes are immobilized in three-dimensional carbon nanotube (CNT) membranes to form CNT/REE extraction bacteria membranes. One method using vacuum filtration to construct CNT membranes is described by Wu et al. (2004) *Science* 305(5688):1273-1276. The vacuum filtration approach enables homogeneity of nanotubes membrane through controlling the permeation rate. Due to the high aspect ratio of CNT, the interpenetrated nanotubes can easily form a network with excellent mechanical integrity, which is critical for many applications. The thickness of CNT membranes can be tuned based on specific requirements by adjusting the loading of CNT powders. Vacuum filtration has been extensively applied to the synthesis of one-or/and two-dimensional nanomaterial-based membranes. In other embodiments, two-dimensional molybdenum disulphide (MoS1)-based film is used. Acerce M. et al. (2015) *Nat. Nanotechnol.* 10(4):313-318. Functional microbes such as REE microbes described herein can be inoculated within the three-dimensional CNT networks. The systems offer flexibility in tuning the properties/performance of the film by varying the ratio of CNT to the microbes. The conductive CNT scaffold also allows electrical and electrochemical measurements of the trapped microbes. FIGS. 15A-C show various scanning electron microscopy images of bacteria containing-CNT membranes.

The genetically engineered microbes provided herein can be provided in a reactor. Reactors can be configured in any suitable arrangement known to one of skill in the art, for example, spiral sheet and fiber brush, column purification, and filtration systems. Operation parameters and modeling that can be optimized by one of skill in the art include, for example, flow rate, extraction efficiency and product purification, solution conditioning (e.g., calcium addition), and surface complexation modeling (SCM) and performance optimization and prediction.

Figure 16:
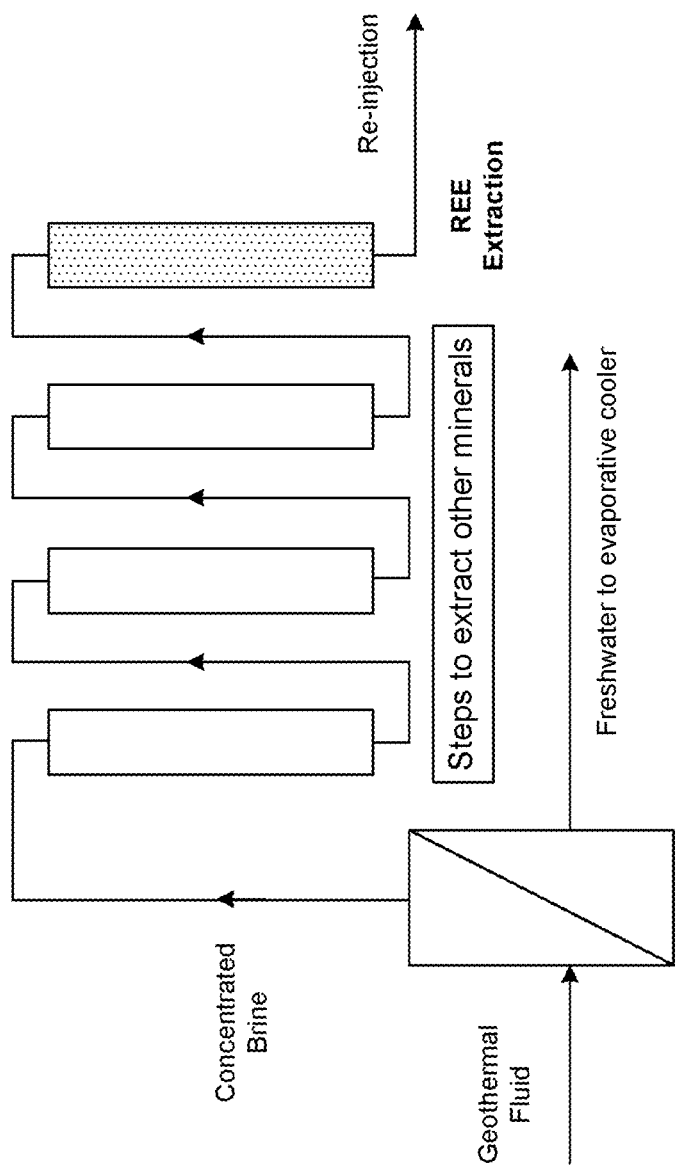
FIG. 16 is a schematic of a system according to one embodiment of the present disclosure incorporated into an existing mineral extraction process.

In some embodiments, systems provided herein can be used in isolation to extract REE from REE-containing material. In other embodiments, the systems provided herein can be outfitted or incorporated into an existing mineral extraction process. For example, FIG. 16 demonstrates one embodiment wherein the REE extraction system provided herein is placed within an existing mineral extraction process for extraction of metals (e.g., Si/Fe, Mn/Zn, and Li) from an aqueous material (e.g., geothermal brine). The REE extraction system can be placed at any stage of an existing extraction process, for example, at the beginning, the middle, or the end. FIG. 16 shows the REE extraction system placed at the end of the process.

Methods

Also provided are methods of using the genetically modified microbes provided herein to extract REE from REE-containing materials and/or detection of the presence or absence of REE (e.g., Tb or Eu) in a material.

In one aspect provided herein are methods for extracting rare earth elements (REE) from a material comprising the steps of: providing genetically engineered microbes comprising an exogenous nucleic acid sequence encoding at least one REE binding ligand; contacting the genetically engineered microbes with a REE containing material, whereupon the REE binding ligand specifically binds at least a portion of the REE to form a microbe-REE complex; and separating the microbe-REE complex from at least a portion of the material. In some embodiments, the steps described are executed once. In other embodiments, the steps or a portion of the steps are executed more than once, for example, 2, 3, 4, 5, or more times.

The material may be any material known to contain or suspected to contain REE. In some embodiments the material is a solid material, a semi-solid material, or an aqueous medium. In a preferred embodiment, the material is an aqueous solution. Non-limiting examples of suitable materials for use in extraction of REE include rare earth ores (e.g., bastnasite, monazite, loparite, and the lateritic ion-adsorption clays), geothermal brines, coal, coal byproducts, mine tailings, phosphogypsum, acid leachate of solid source materials, REE solution extracted from solid materials through ion-exchange methods, or other ore materials, such as REE containing clays, volcanic ash, organic materials, and any solids/liquids that react with igneous rocks.

The genetically engineered microbes can also be used for recovering REE from recycled REE-containing products such as, compact fluorescent light bulbs, electroceramics, fuel cell electrodes, NiMH batteries, permanent magnets, catalytic converters, camera and telescope lenses, carbon lighting applications, computer hard drives, wind turbines, hybrid cars, x-ray and magnetic image systems, television screens, computer screens, fluid cracking catalysts, phosphor-powder from recycled lamps, and the like. These materials are characteiized as containing amounts of REE, including, for example, scandium, yttrium, lanthanum, cerium, praseodymium, neodymium, samarium, promethium, europium, gadolinium, terbium, dysprosium, erbium, thulium, ytterbium, lutetium, or any combination thereof.

In some embodiments, the material is pre-processed prior to providing the genetically engineered microbes. Non-limiting examples of suitable pre-processing includes acid leaching, bioleaching, ion-exchange extraction, pH adjustment, iron oxide precipitation, temperature cooling (e.g., geothermal brines). In other embodiments, prior to providing the genetically engineered microbes, the REE containing material is refined to remove at least a portion of non-REE metals. In some embodiments, the non-REE metals are extracted using microbes, for example, genetically modified or unmodified *C. crescentus*.

In some embodiments, an additive is added to increase the binding affinity of a REE to the REE binding ligand. In one embodiment, the additive is calcium salt.

In some embodiments, at least a portion of the genetically engineered microbes are attached (i.e., immobilized) to a surface of a solid support prior to contacting with a REE containing material. It is contemplated that microbe immobilization in biosorption medium for use in flow-through setups allows for complete (or substantially complete) separation of REEs from REE-containing mixed metal solutions in a single step. In one embodiment, about 20%, about 30%, about 40%, about 50%, about 60%, about 70%, about 80%, about 90%, about 91%, about 95%, about 97%, about 98%, about 99%, or 100% of the REE in the REE-containing material (e.g., mixed metal solution) is extracted in a single step. In some embodiments, about 1%, 5%, 10%, 15%, 20%, about 30%, about 40%, about 50%, about 60%, about 70%, about 80%, about 90%, about 91%, about 95%, about 97%, about 98%, about 99%, or 100% more of the REE in the REE-containing material (e.g., mixed metal solution) is extracted in a single step as compared to an amount of REE extracted in a single step using conventional extraction methods.

The binding of REE to the genetically engineered microbes can be reversible. In some embodiments, at least a portion of the REE in the microbe-REE complex is desorbed (i.e., removed or separated) from the microbes. Non-limiting examples of suitable methods include acid treatment (e.g., sulfuric acid/HNO$_3$ and HCl), citrate, acetate, gluconate, and heat treatment. In a preferred embodiment, the removal step is performed by acid-stripping. In another preferred embodiment, wherein the removal step is performed using an amount of citrate. In yet another preferred embodiment, wherein the removal step is performed using heat treatment.

The genetically engineered microbes can also be reused. In some embodiments, the methods further comprise removing the REE from the genetically engineered microbes to regenerate genetically engineered microbes. The genetically engineered microbes provided herein can be used 2, 3, 4, 5, 6, 7, 8, 9, 10, 15, 20, 25, 30, or more times. In other embodiments, the genetically engineered microbes are single use. The microbes can be re-conditioned by any means known to one of skill in the art. For example, the microbes may be cleaned with buffer to wash off the citrate to re-generate microbes. In one embodiment, the methods further comprise reusing the regenerated genetically engineered microbes to carry out the extraction of REE from REE-containing material.

EXAMPLES

Example 1: Generation of Genetically Engineered *Caulobacter crescentus* Expressing Lanthanide Binding Tag To effectively adsorb REEs from metal ion mixtures, *C. crescentus* S-layer protein was modified to display LBTs on the cell surface. Briefly, to generate p4ArsaA(723Δ)-dLBTx1, dLBT, a double lanthanide tag containing a tandem copy of sLBT3 (Martin, L. J. et al., *J. Am. Chem. Soc.* 2007, 129 (22) 7106-7113) was PCR amplified using primers dLBT1 (SEQ ID NO. 1) and dLBT2 (SEQ ID NO. 2). Using InFusion cloning (Clontech In-Fusion HD Cloning Plus kit, Mountain View, Calif., USA), the dLBT product was inserted at amino acid position 723 of rsaA in the plasmid p4ArsaA(723Δ)GSCCΔ that was linearized using primers dLBT3 and dLBT4. The sequence of cloned regions was confirmed by sequencing.

The number of dLBT copies within rsaA was exponentially increased following the method as described in Nomellini et al., *Appl. Environ. Microbiol.* 2007, 73 (10) 3245-3253. A synthetic dsDNA fragment containing a tandem repeat of dLBT3 and the Muc1B spacer with BglII and SpeI sites on the 5' end and NheI and PstI sites on the 3' end was digested with BglII and PstI and cloned into the similarly digested p4ArsaA(723Δ)GSCCΔ, yielding p4ArsaA(723Δ)-dLBTx2-Muc1B. To construct p4ArsaA (723Δ)-dLBTx4-Muc1B, the larger fragment from an NheI/HindIII digest of p4ArsaA(723Δ)-dLBTx2-Muc1B was ligated to the smaller fragment of a SpeI/HindIII digest of the same plasmid. p4ArsaA(723Δ)-dLBTx8-Muc1B (dLBTx8: SEQ ID NO. 9) was constructed by the similarly digesting and ligating p4ArsaA(723Δ)-dLBTx4-Muc1B (dLBTx4: SEQ ID NO. 8). Plasmids were transformed into *C. crescentus* strain CB2A by electroporation. See Table 2 for a list of the strains and plasmids used.

TABLE 2

Strains and plasmids

| Strains/Plasmids | Description |
| --- | --- |
| Strains | |
| JS4022[a] | *C. crescentus* CB2A Sap⁻ (point mutation) recA repBAC⁺ derivative of JS4015 |
| | JS4022/p4ArsaA(723Δ)GSCCΔ |
| DP58 | JS4022/p4ArsaA(723Δ)dLBTx1 |
| DP128 | JS4022/p4ArsaA(723Δ)dLBTx2-Muc1B |
| DP146 | JS4022/p4ArsaA(723Δ)dLBTx4-Muc1B |
| DP152 | JS4022/p4ArsaA(723Δ)dLBTx8-Muc1B |
| DMP268 | MG1655 pBAD-ompA-dLBT2x |
| DMP269 | MG1655 pBAD-lpp-ompA-dLBT4x |
| DMP280 | MG1655 pBAD-ompA-dLBT8x |
| DMP281 | MG1655 pBAD-lpp-ompA-dLBT8x |
| DMP468 | ΔlpxT pBAD-lpp-ompA-dLBT8x |
| DMP489 | W3110 pBAD-lpp-ompA-dLBT8x |
| DMP488 | WD101 pBAD-lpp-ompA-dLBT8x |
| Plasmids | |
| p4ArsaA(723Δ)GSCCΔ[a] | p4A containing rsaAΔP with a segment containing several unique restriction sites inserted at the BamHI linker site corresponding to aa 723 of RsaA; Cm$^R$ |
| $P_{BAD}$-ompA-pbrR[b] | |
| $P_{BAD}$-lpp-ompA-pbrR[b] | |
| p4ArsaA(723Δ)dLBTx1 | p4A containing rsaAΔP with dLBT inserted into the BglII and SpeI sites of p4ArsaA(723Δ)dLBT; Cm$^R$ |
| p4ArsaA(723Δ)dLBTx2-Muc1B | p4A containing rsaAΔP with dLBTx2-Muc1B inserted into the BglII and SpeI sites of p4ArsaA(723Δ)dLBT; Cm$^R$ |
| p4ArsaA(723Δ)dLBTx4-Muc1B | p4A containing rsaAΔP with dLBTx4-Muc1B inserted into the BglII and SpeI sites of p4ArsaA(723Δ)dLBT; Cm$^R$ |
| p4ArsaA(723Δ)dLBTx8-Muc1B | p4A containing rsaAΔP with dLBTx8-Muc1B inserted into the BglII and SpeI sites of p4ArsaA(723Δ)dLBT; Cm$^R$ |
| $P_{BAD}$-ompA-dLBTx2 | C-terminal fusion of dLBT2x to OmpA under control of the arabinose inducible promoter ($P_{BAD}$); AP$^R$ |
| $P_{BAD}$-lpp-ompA-dLBTx2 | C-terminal fusion of dLBT2x to Lpp-OmpA under control of the arabinose inducible promoter ($P_{BAD}$); AP$^R$ |
| $P_{BAD}$-ompA-dLBTx4 | C-terminal fusion of dLBT4x to OmpA under control of the arabinose inducible promoter ($P_{BAD}$); AP$^R$ |
| $P_{BAD}$-lpp-ompA-dLBTx4 | C-terminal fusion of dLBT4x to Lpp-OmpA under control of the arabinose inducible promoter ($P_{BAD}$); AP$^R$ |
| $P_{BAD}$-ompA-dLBTx8 | C-terminal fusion of dLBT8x to OmpA under control of the arabinose inducible promoter ($P_{BAD}$); AP$^R$ |
| $P_{BAD}$-lpp-ompA-dLBTx4 | C-terminal fusion of dLBT8x to Lpp-OmpA under control of the arabinose inducible promoter ($P_{BAD}$); AP$^R$ |

[a]Nomellini et al., *Appl. Environ. Microbiol.* 2007, 73 (10) 3245-3253
[b]Wei, W. et al., *Environ Sci Technol* 2014, 58(6) 3363-3371

*C. crescentus* CB2A was grown at 30° C. in PYE (Park, D. M. et al., *Appl. Environ. Microbiol.* 2014, 80 (18) 5680-8) with 1 μg mL$^{-1}$ chloramphenicol. PYE was supplemented with 2.5 mM CaCl$_2$ for strain dLBTx4 and 2.5 mM CaCl$_2$ and 2 mL L$^{-1}$ Hutner's trace metal solution (Hutner, S. H. et al., *Proc. Am. Philos. Soc.* 1950, 94, 152-170) for strain dLBTx8. Overnight cultures were grown to late exponential phase prior to harvesting for REE adsorption assays. For S-layer extraction studies, assembled S-layers were extracted using HEPES pH 2.0 buffer as previously described in Walker, S. G., et al., *J. Bacteriol.* 1992, 174 (6) 1783-92 and analyzed by SDS-PAGE (7%).

Figure 1B:
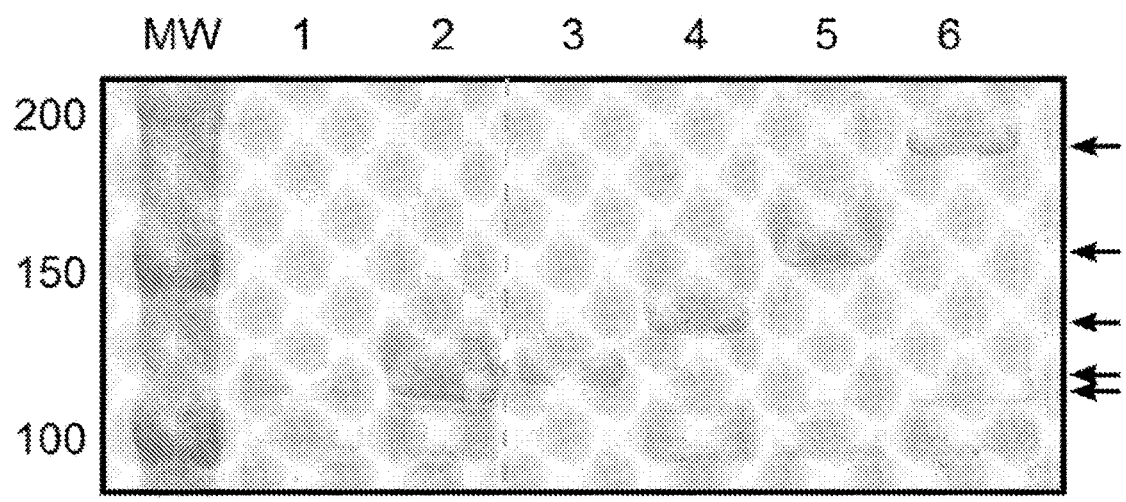
FIG. 1B is a representative image of a SDS-PAGE of S-layer extracted from the following strains: (1) wild type CB2A, (2) CB2A rsaA (control), (3) dLBTx1, (4) dLBTx2, (5) dLBTx4, and (6) dLBTx8. dLBTx4 and dLBTx8 cells were grown in PYE medium supplemented with additional $Ca^{2+}$ (2.5 µM) and $Ca^{2+}$ (2.5 µM) with trace metals, respectively. MW; molecular weight (kDa) markers. Arrows on the right indicate the engineered RsaA protein expressed from each strain.

A double LBT (hereafter dLBT) comprised of tandem sLBT3 (Martin, L. J. et al., *J. Am. Chem. Soc.* 2007, 129 (22) 7106-7113) was inserted into the S-layer gene, rsaA, yielding strain dLBTx1 (FIG. 1A). Extraction and visualization of S-layer protein from strain dLBTx1 indicated that the fusion protein was displayed on the cell surface (FIG. 1B, lane 3).

To further improve REE adsorption capacity, the copy number of dLBT within RsaA was increased exponentially up to 8 copies resulting in strains dLBTx2, dLBTx4, and dLBTx8 (FIG. 1A). Duplication of dLBT (strain dLBTx2) did not perturb S-layer formation or cell growth. However, both the dLBTx4 and dLBTx8 strains exhibited an S-layer shedding phenotype accompanied by lower growth yields (data not shown). In an attempt to reduce S-layer shedding, growth medium was supplemented with additional Ca$^{2+}$ (2.5 μM). The results showed that Ca$^{2+}$ addition restored normal growth yield (Data not shown) and S-layer production for the dLBTx4 strain (FIG. 1B, lane 5). Although some improvement was observed for strain dLBTx8 with the addition of Ca$^{2+}$ and trace metals, significant S-layer shedding still occurred, resulting in reduced S-layer production as shown by the fainter S-layer band (FIG. 1B, lane 6).

Example 2: Adsorption of RRE onto LBT-Displayed Microbes

As one of the five REEs of highest criticality (DOE, Critical Materials Strategy. www.energy.gov, 2011), Tb$^{3+}$ adsorption onto the cell surface-displayed LBTs was first examined. Conveniently, LBTs contain a strategically placed tryptophan residue that sensitizes Tb-luminescence, allowing Tb binding to surface-displayed LBTs to be assessed through luminescence measurements. Nitz, M. et al., *Angew. Chem., Int. Ed.* 2004, 43 (28) 3682-3685.

Briefly, for the luminescence titration experiments, overnight cultures were washed once and resuspended in 10 mM MES (2-(N-morpholino)ethanesulfonic acid) buffer pH 6.1 and 10 mM NaCl to a final density of 8×108 cells/ml). A Tb$^{3+}$ stock solution (50 mM) was prepared by dissolving ThCl$_3$ hydrate salts (Sigma-Aldrich) in 100 mM HCl, and a Ca$^{2+}$ stock solution (1 M) was prepared by dissolving CaCl$_2$) in ddH$_2$O. Cells were incubated with varying Tb$^{3+}$ concentrations for 20 min prior to luminescence measurements (Ex/Em 280/544 nm) using a 96-well plate reader (Biotek, Winooski, Vt., USA). Nitz, M. et al., *Angew. Chem., Int. Ed.* 2004, 43 (28) 3682-3685.

For competition experiments, 50 mM stock solutions of DyCl$_3$, EuCl$_3$, La(NO$_3$)$_3$, Nd acetate, YCl$_3$, YbCl$_3$, CeCb, and FeCl$_3$ were prepared in 1 mM HCl and 50 mM stock solutions of NiSO$_4$, ZnSO$_4$, CuSO$_4$, MnCl$_2$, MgSO$_4$, CoCl$_2$, and AlK(SO$_4$)$_2$ were prepared in ddH$_2$O. Cells were initially loaded with 10 μM Tb$^{3+}$ by incubation in Tb binding solution (10 mM MES pH 6.1, 10 mM NaCl, 10 μM TbCl3) in the presence of 150 mM Ca$^{2+}$ and luminescence was measured after 20 min. Aliquots of each metal stock were then added and luminescence was measured following a 5 min incubation. Min-Max normalization was used to normalize the luminescence data to the 0-1 range using the luminescence signal of dLBTx4 incubated with 10 μM Tb$^{3+}$ as 1 and the luminescent signal of dLBTx4 with no Tb$^{3+}$ as 0. Titration data were analyzed and IC50 values determined using the drc (dose response curve) package of R.(43) The dissociation constant (K$_d$) for the binding of each REE to LBTs was calculated from the IC50 value using the Cheng-Prusoff equation. Cheng, Y. et al., *Biochem. Pharmacol.* 1973, 22 (23) 3099-3108:

$$K_d = \frac{IC_{50}}{(1 + [L]/K_b)}$$

where L is the concentration of Tb$^{3+}$ (10 μM), and K$_b$ is the binding affinity of LBT for Tb$^{3+}$ calculated based on luminescence titrations.

For Tb$^{3+}$ desorption experiments, 100 mM stocks (pH 6) of sodium acetate, sodium citrate and sodium gluconate were prepared. Cells were incubated in Tb binding solution with or without 100 mM CaCl$_2$ and then subjected to various concentrations of the organic acids. Luminescence was measured after 20 min and normalized as described above.

Figure 2A:
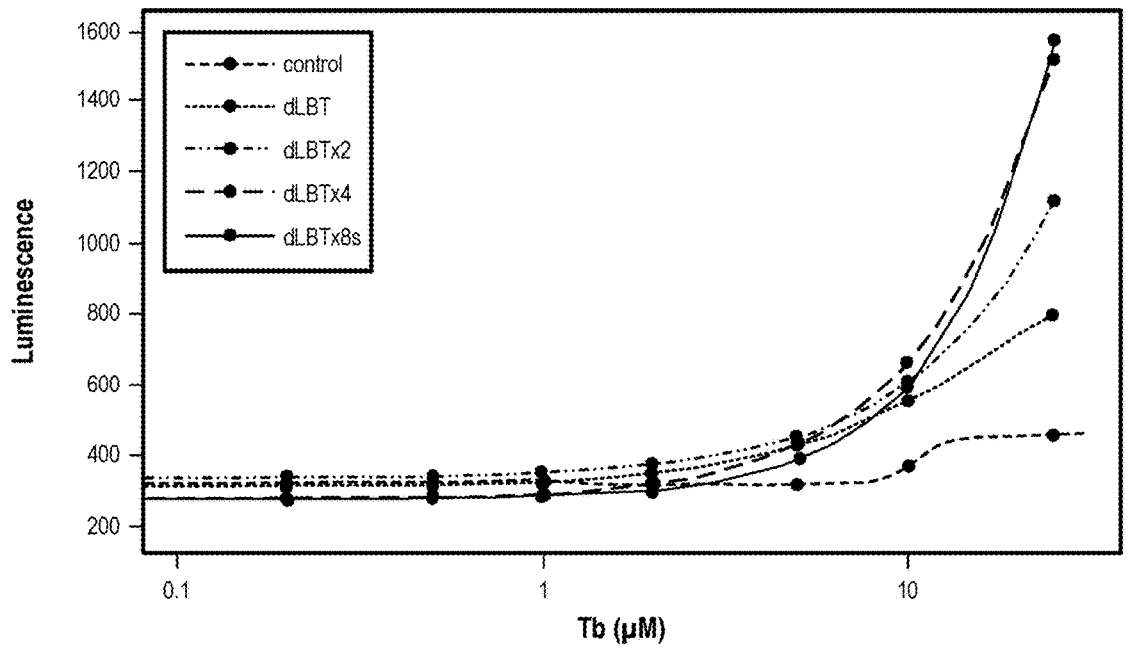

As shown in FIG. 2A, strain dLBTx1. exhibited increased luminescence compared to a strain that expressed S-layer protein lacking dLBT (hereafter control strain), suggesting that surface-displayed dLBT was capable of binding Tb$^{3+}$. Moreover, the luminescence intensity increased with increasing number of dLBT up to four copies, suggestive of greater Tb$^{3+}$ binding capacity. The luminescence intensity was not significantly improved in strain dLBTx8, likely due to S-layer shedding. Therefore, strain dLBTx4 was chosen for all subsequent experiments, unless specified otherwise.

To confirm. REE adsorption, suggested by luminescence measurements, Tb$^{3+}$ adsorption was quantified using ICP-MS. For these studies, REE binding experiments were performed as described above for luminescence titrations. For adsorption experiments at a pH other than 6, MES buffer was replaced with 5 mM acetate buffer (pH 5, 4.5, 4). After REE adsorption, cells were centrifuged at 20 000 g for 8 min, and the supernatant was extracted. Ultrapure concentrated nitric acid was used to acidify (1% v/v) the samples and the commercial standard stock solutions prior to inductively coupled plasma mass spectrometry (ICP-MS) analysis. The instrument (iCAP Q, ThermoFischer Scientific, Carlsbad, Calif., USA) was standardized and operated in accordance with manufacturer's instructions. Total adsorbed REE was calculated by subtracting the REE concentration remaining in the supernatant from the concentration of REE in the control without bacterial cells.

Figure 2B:
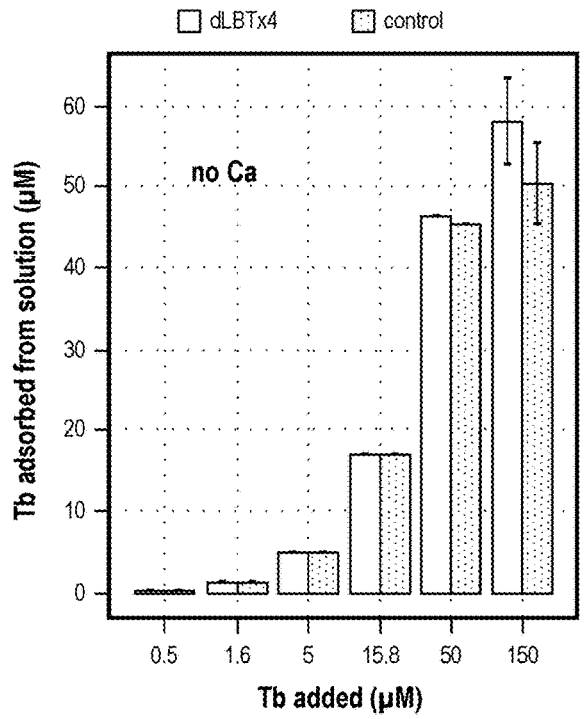

Initial measurements showed similar Tb$^{3+}$ adsorption between dLBTx4 and the control strain at all Tb$^{3+}$ concentrations tested (FIG. 2B). Both strains adsorbed up to ~6.25×10$^{-8}$ nmole Tb$^{3+}$ per cell, equating to 50 μM of Tb$^{3+}$ at a cell concentration of 8×10$^8$ cells per mL. A variety of other bacteria and algae species including *E. coli*, *Bacillus subtilis*, and *Pseudomonas* species have been reported to adsorb REEs (e.g., Eu, Yb, and Dy), with adsorption ranging from 1 to 100 μM at similar cell concentrations. Moriwaki, H. et al., *Appl. Microbial. Biotechnol.* 2013, 97 (1) 1-8; Texier, A. C. et al., *Environ. Sci. Technol.* 1999, 33 (3) 489-495; Tsuruta, T., J., *Rare Earths* 2007, 25 (5) 526-532; Ozaki, T. et al., Radiochim. Acta 2004, 92 (9-11) 741-748;

Jiang, M. Y. et al., Cosmochim. Acta (2012) 93, 30-46; Kuroda, K. et al., Appl. Microbial. Biotechnol. 2010, 87 (1) 53-60; Lo, Y. C. et al., Bioresour. Technol. 2014, 160, 182-190. The adsorption of rare earth ions by these native microbial systems is mediated by the presence of functional groups (e.g., phosphates and carboxyls) on the cell wall as well as through the cellular release of inorganic phosphate. Gadd, G. M., Microbiology 2010, 156 (3) 609-43; Jiang, M. Y., et al., Geochim. Cosmochim. Acta 2012, 93, 30-46. Although the background cell wall adsorption of $Tb^{3+}$ may serve to further increase the REE binding capacity, it is unlikely to possess the same level of specificity for REE that is characteristic of LBTs. As such, cell wall adsorption is likely undesirable for the purpose of REE enrichment.

Figure 2C:
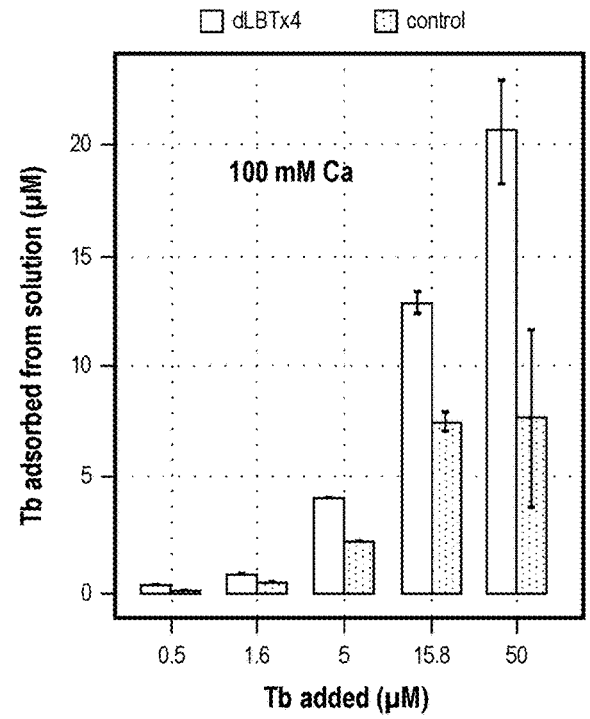
Figure 5:
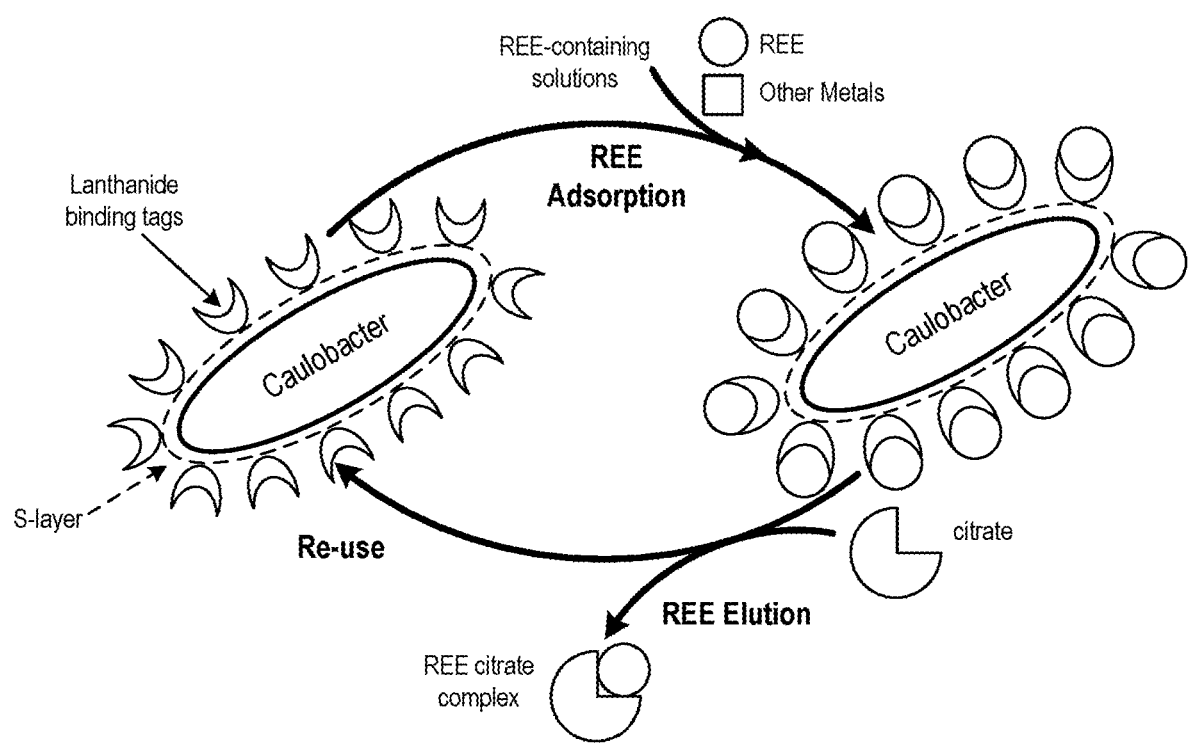
FIG. 5 is a schematic representation of a genetically engineered microbe according to an embodiment of the present disclosure, extraction of REE from REE-containing solutions, and recycling of the microbe.

To mitigate the background ion adsorption, $Ca^{2+}$ was added as a competitor. Rare earth ions and $Ca^{2+}$ have a similar ionic radius and oxophilicity (Bunzli, J. C., Acc. Chem. Res. 2006, 39 (1) 53-61), and a previous report suggested that excess $Ca^{2+}$ blocks the formation of $Tb^{3+}$ deposits on the bacterial membrane. (Bayer, M. E. et al., J. Bacteriol. 1991, 173 (1) 141-149). Furthermore, Ca is a common metal present in REE-containing source materials. (Jones, A. P. et al., Rare Earth Minerals: Chemistry Origin and Ore Deposits. Chapman & Hall: London, 1996. With 100 mM $Ca^{2+}$, although overall $Tb^{3+}$ adsorption ($2.6 \times 10^{-8}$ nmol/cell capacity for dLBTx4) was lower compared to conditions with no added $Ca^{2+}$, dLBTx4 adsorbed a significantly greater amount of $Tb^{3+}$ compared to the control at all tested $Tb^{3+}$ concentrations (FIGS. 2C and 2E). This suggested that while the vast majority of non-LBT sites on the cell wall were occupied by $Ca^{2+}$ the REE-selective LBT sites were still available for $Tb^{3+}$ binding. Consequently, a significant increase in apparent binding affinity of LBT for $Tb^{3+}$ was observed in all engineered strains (FIG. 2D). Higher $Ca^{2+}$ concentrations beyond ~100 mM did not further decrease background cell wall binding (FIG. 2E), and thus, 100-150 mM $Ca^{2+}$ was used in the subsequent metal adsorption experiments described below. The absence of a $Ca^{2+}$ effect on $Tb^{3+}$ adsorption by dLBTx4 in FIG. 2E is indicative of excess LBT relative to added $Tb^{3+}$ (10 µM), while FIG. 2C suggests that at the cell concentrations used in these assays, surface displayed LBT can adsorb $12.9 \pm Tb^{3+}$.

Given the poor solubility of REEs at neutral and alkaline pH and the fact that REE-containing aqueous solutions during REE processing tend to be acidic (Zhuang, W. Q. et al., Curr. Opin. Biotechnol. 2015, 33, 327-335; Xie, F. et al., Miner. Eng. 2014, 56, 10-28), REE adsorption within the pH range of 4-6 was evaluated (FIG. 2F). $Tb^{3+}$ adsorption to dLBTx4 was maximal at pH 6 (93% of Tb added), reduced to ~60% at pH 5 and to ~40% at pH 4.5 and 4. Minimal adsorption was observed below pH 4 as evidenced by luminescence measurements (data not shown). Thus, LBT-displayed cells are most effective in a pH range of 5-6.

Example 3: REE Adsorption Specificity

Since REE sources frequently coexist with other metal contaminants in both ores and recycled materials (Binnemans, K. et al., J. Cleaner Prod. 2013, 51, 1-22), $Tb^{3+}$ adsorption in the presence of various metal ions was evaluated. Competition experiments were performed by loading LBTx4 cells with $Tb^{3+}$ followed by monitoring the decrease in luminescence intensity in response to increasing concentrations of other metal ions (FIG. 3A). LBTx4 displayed high selectivity for $Tb^{3+}$ over other metal ions tested. With the exception of $Cu^{2+}$, addition of metal ions up to at least 100 µM, an order of magnitude higher than the $Tb^{3+}$ concentration, had minimal effect on $Tb^{3+}$ binding. Given that $Cu^{2+}$ was the most effective competitor based on luminescence, $Tb^{3+}$ adsorption was quantified by ICP-MS in the presence of $Cu^{2+}$ (FIG. 3B). In agreement with the luminescence data, higher $Cu^{2+}$ concentrations (1 mM) were inhibitory for $Tb^{3+}$ adsorption. However, the results observed with 100 µM $Cu^{2+}$ were inconsistent between the two measurement methods: nearly 100% $Tb^{3+}$ adsorption was measured by ICP-MS, whereas a 60% reduction in luminescence was observed, which could be due to luminescence quenching by $Cu^{2+}$. (Rahimi, Y. et al., Biochem. Biophys. Res. Commun. 2008, 370 (1) 57-61). Overall, the weak affinity of surface displayed LBTs for non REE metal ions suggests that REE adsorption is largely unaffected by the presence of commonly occurring metal ions in source materials, at least at concentrations up to 100-fold higher than REEs.

Figures 6A, 6B:
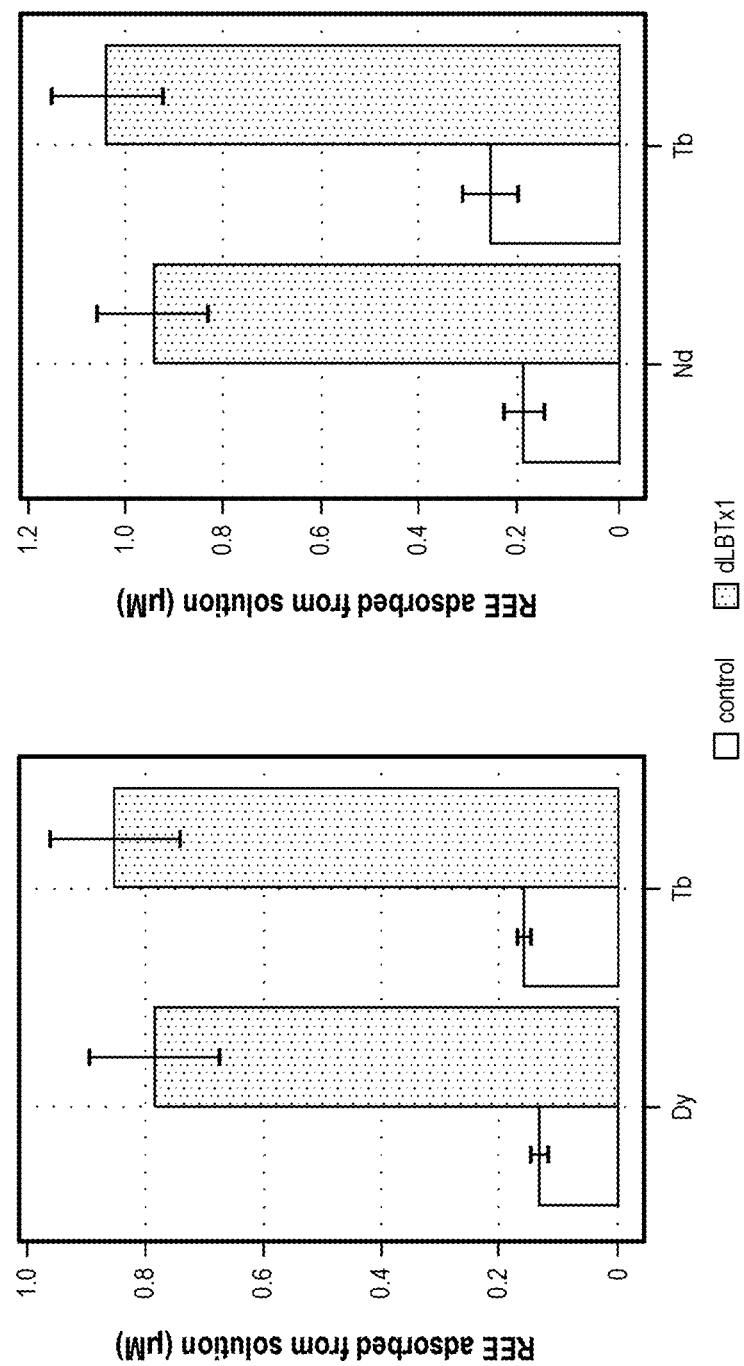
FIGS. 6A-6B REE adsorption by dLBTx1 and control strains incubated with 1.6 µM each of Dy and Tb (FIG. 6A) or Nd and Tb (FIG. 6B) in the presence of 150 mM $Ca^{2+}$.
Figure 7A:
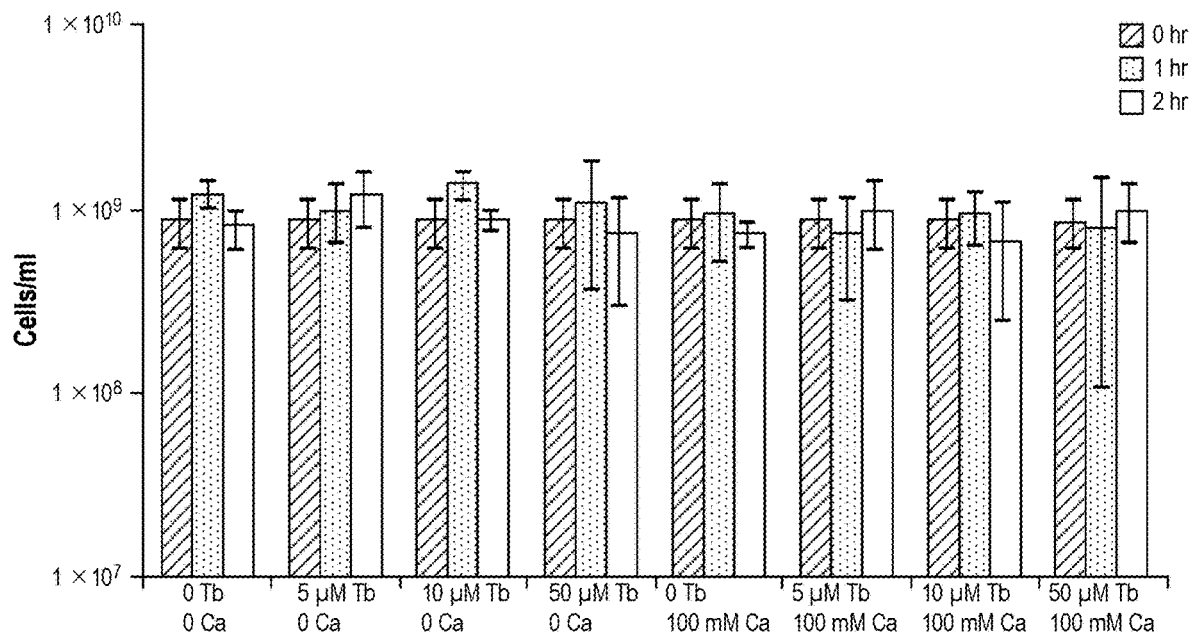
FIGS. 7A-7B show cell survival during Tb adsorption. Control cells lacking LBT (FIG. 7A) or dLBTx4 cells (FIG. 7B) were exposed to 0, 5, 10 or 50 µM Tb in the presence or absence of 100 mM $Ca^{2+}$ and colony forming units (per milliliter) were determined after 0, 1 and 2 h incubation. Error bars represent standard deviations of three biological replicates.
Figure 7B:
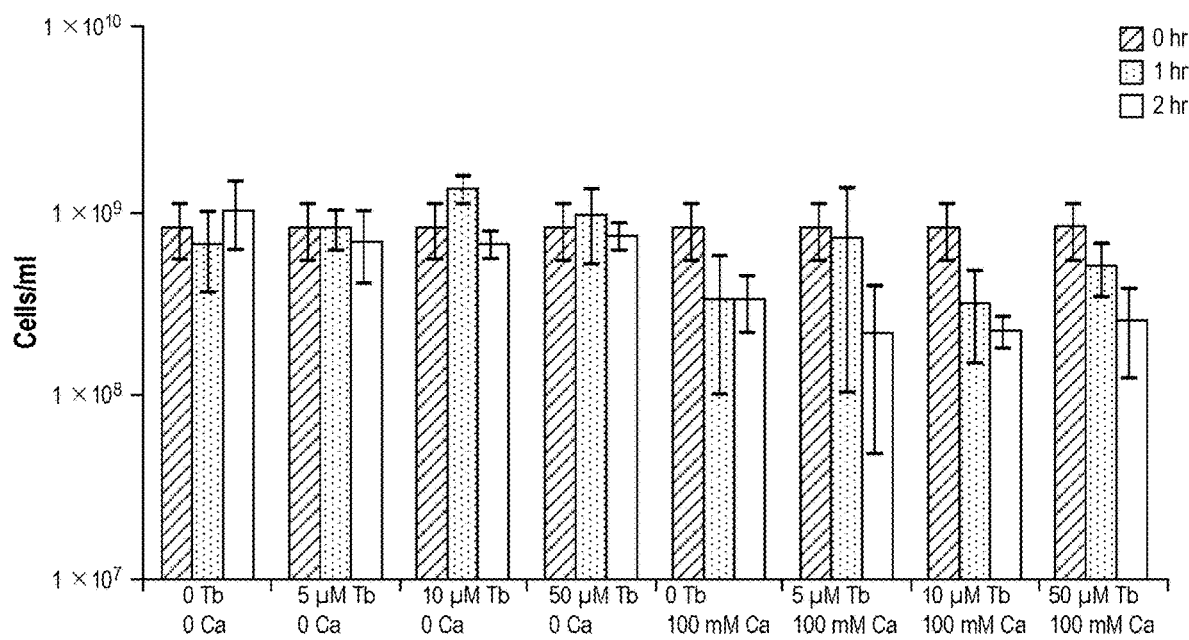
Figure 8:
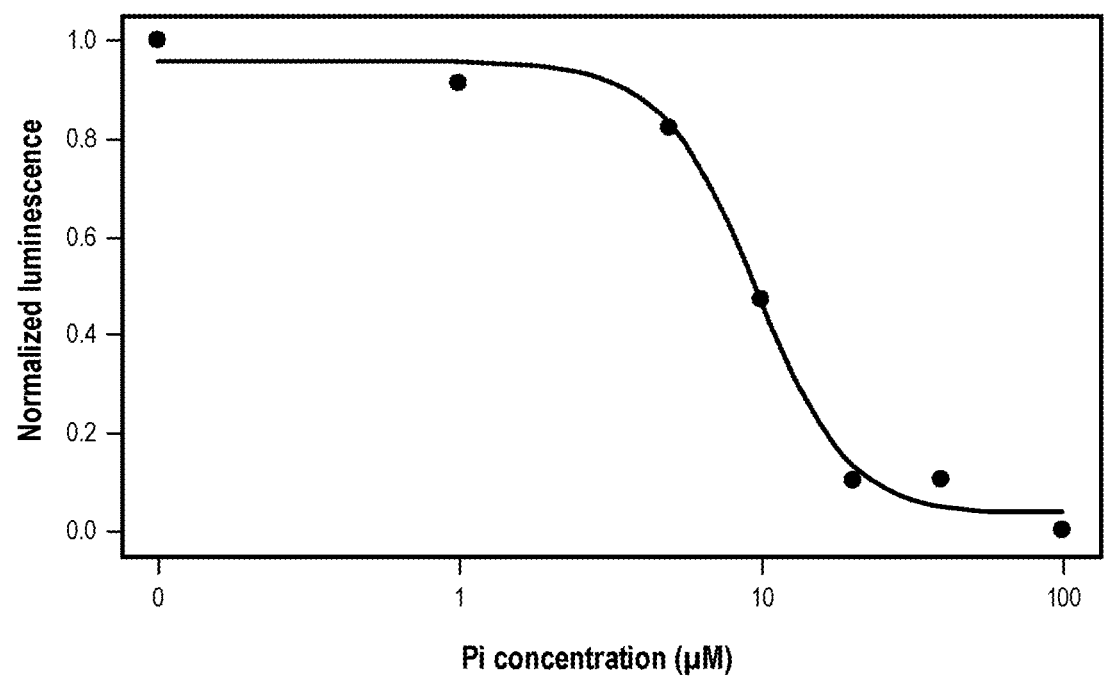
FIG. 8 shows competition experiments with dLBTx4 cells preloaded with 10 µM $Tb^{3+}$ followed by addition of $KH_2PO_4$ (Pi) at concentrations up to 100 µM. Normalized luminescence was calculated as described below.

Experiments were also conducted to determine adsorption selectivity among REEs. Due to their similar physiochemical properties, it is very difficult to chemically separate REEs from one another, often requiring dozens of organic solvent extraction steps. (Xie, F., Miner. Eng. 2014, 56, 10-28). Competition binding experiments revealed that dLBTx4 preferred REEs with smaller atomic radii (FIG. 3C; Table 3), similar to results with LBT peptides in solution. (Nitz, M., et al., Angew. Chem., Int. Ed. 2004, 43 (28) 3682-3685). $Eu^{3+}$, $Dy^{3+}$, and $Yb^{3+}$ were all effective competitors of $Tb^{3+}$, with binding affinities of ~3 µM, whereas $Y^{3+}$ and $Nd^{3+}$ were slightly poorer competitors. $La^{3+}$ and $Ce^{3+}$, with the largest atomic radii among REEs, were the weakest substrates for LBT. Consistent with this data, ICP-MS measurements of REE adsorption in the presence of equimolar $Tb^{3+}/Dy^{3+}$ or $Tb^{3+}/Nd^{3+}$ mixtures revealed no significant preference for one REE over the other (FIGS. 6A-6B). In contrast, $Tb^{3+}$ was preferentially adsorbed over $La^{3+}$ when both REEs were present in equimolar concentrations (FIG. 3D). Overall, these results suggest that the LBT-displayed strains have the potential to selectively enrich for REEs with smaller radii, including all five REEs of high criticality. This is an important feature given the high relative abundance of La and Ce in many REE source materials. (Binnemans, K. et al., J. Cleaner Prod. 2013, 51, 1-22).

TABLE 3

| REE Specificity of Strain dLBTx4 | |
| --- | --- |
| REE | $K_D$ (µM) |
| Eu | 2.5 (0.2)[a] |
| Yb | 3.1 (0.3) |
| Dy | 3.2 (0.7) |
| Tb | 3.8 (0.3) |
| Y | 5.7 (0.1) |
| Nd | 13.3 (3.8) |
| Ce | 114 (53) |
| La | 153 (55) |

[a]Numbers in parentheses represent standard deviations of 3 replicates.

Example 4: Desorption of REE from Engineered Microbes

Since the ability to reuse the engineered cells for metal adsorption would lower the cost associated with cell regeneration for industrial applications, REE desorption and subsequent readsorption (recycling) studies established a general strategy for REE recovery. A variety of chemicals including acids, salts, and ligands have been used for metal desorption from environmental surfaces. (Lo, Y. C. et al., *Bioresour. Technol.* 2014, 160, 182-190). In particular, some organic acids such as citric acid are able to form strong complexes with REEs. (Goyne, K. W. et all., *Chem. Geol.* 2010, 278 (1-2) 1-14.

For studying adsorption/desorption cycling, cells were incubated in Tb binding solution containing 150 nM. $CaCl_2$ and luminescence was measured after 20 min. Citrate was added to 5 mM for 5 min before cells were centrifuged at 20 000 g for 8 min. $Tb^{3+}$ in the supernatant was quantified as described above. The total $Tb^{3+}$ in a solution lacking cells was used to calculate the fraction of eluted $Tb^{3+}$. The cell pellet was washed with 10 mM MES pH 6.1 to eliminate residual citrate, centrifuged, and suspended in Tb binding solution containing 100 mM $CaCl_2$). Luminescence was measured after 5 min and normalized by the optical density at 600 nm ($OD_{600}$) to account for any loss in cell density during wash steps. Fractional saturation was determined as described above. Citrate elution followed by $Tb^{3+}$ reloading was repeated twice.

It was discovered that $Tb^{3+}$ was fully recovered from the dLBTx4 cell surface with 1-5 mM citrate (FIG. 4A). In contrast, acetate or gluconate were much less effective, even at much higher concentration (45 mM; FIG. 4A). A higher concentration of organic acids was required when $Ca^{2+}$ was present in the reaction mixture, presumably due to complexation of the organic acids with $Ca^{2+}$ (see discussion below). Importantly, the REE adsorption capacity is fully maintained over at least two rounds of citrate-mediated desorption (FIG. 4B). Furthermore, cell viability was not significantly affected by $Tb^{3+}$ adsorption (FIGS. 7A-7B), suggesting that $Tb^{3+}$ is not toxic on the time scale of adsorption experiments. The rapid and reversible nature of REE-cell binding should facilitate efficient recovery of REEs, alleviating the need for cell regeneration between extraction rounds.

Thermodynamic speciation analysis based on the Mixed-Solvent Electrolyte (MSE) thermodynamic model (Wang, P. et al., *J. Mol. Liq.* 2006, 125 (1) 37-44; Wang, P. et al., *Fluid Phase Equilib.* 2002, 203 (1-2) 141-176) was used to quantitatively rationalize $Tb^{3+}$ desorption by the organic acids. Briefly, Equilibrium speciation calculations were performed with the previously developed Mixed-Solvent Electrolyte (MSE) thermodynamic model. The necessary parameters of the MSE model were determined to reproduce the experimental thermodynamic data for solutions containing Tb, Ca, citrates, and acetates as a function of pH. The individual $Tb^{3+}$ species present in the aqueous solution in the presence of acetate or citrate are shown in FIG. 11A and FIG. 11B, respectively.

If the desorption of $Tb^{3+}$ is attributed to the complexation with organic acids in solution, then the amount of $Tb^{3+}$ desorbed should be proportional to $Tb^{3+}$ complexed in solution. As shown in FIGS. 4C and 4D, the predicted fraction of uncomplexed $Tb^{3+}$ decreased with increasing organic acid concentration, corresponding with the observed decrease in the fraction of $Tb^{3+}$ bound to dLBTx4 (FIG. 4A). It is also evident that citrate is a much stronger complexant of $Tb^{3+}$ than acetate (FIGS. 4C and 4D). Specifically, complexation of $Tb^{3+}$ with citrate is predicted to occur over a narrow range of citrate concentrations with 10 μM sufficient to complex almost all $Tb^{3+}$. In contrast, more than 45 mM acetate was predicted to be required to complex the majority of $Tb^{3+}$ and only at high pH (cf. pH=6.1 in FIG. 4C). Additionally, the predicted complex formation between $Ca^{2+}$ and acetate or citrate explains, at least in part, the requirement for greater concentrations of these organic acids for $Tb^{3+}$ desorption in the presence of $Ca^{2+}$, as shown in FIG. 4A. This $Ca^{2+}$ effect on desorption can also be attributed to the increased apparent binding affinity of LBT for $Tb^{3+}$ in the presence of $Ca^{2+}$ (FIG. 2D).

Example 5: REE Adsorption from Sediment Core Samples from a Prospective REE Mine As a preliminary step toward application, REE adsorption from the acid leachate of core samples collected from the Bull Hill Mine was tested. The high relative abundance of Nd, a REE of high criticality, and the low phosphate concentrations are attractive features for bioadsorption at near neutral pH.

Here, REEs from Bull Hill borehole samples (43.5 m below land surface; Rare Element Resources, Sundance, Wyo., U.S.A.) were leached using aqua regia as follows: 300 mg of sample and 5 mL Milli-Q water were combined with 1.8 ml. HCl and 700 μL of $HNO_3$ in a glass beaker. The beaker was covered with a watch glass and heated at 125° C. for 8 h. An additional 5 mL of Milli-Q water was added, and the heating step was repeated once. The total volume was adjusted to 30 mL with Milli-Q water, and the pH was adjusted to 4.8. Insoluble precipitates were removed by centrifugation at 7000 g for 10 min followed by filtration using a 0.2 μm filter and soluble REEs were quantified by ICP-MS. For LBT binding reactions, the extracted REE solution was diluted 100-fold so that no individual REE exceeded 20 and then adjusted to pH 6 using 10 mM MES. REE concentrations in excess of the dLBTx4 binding capacity were used to determine whether there was preferential adsorption of any REE. Strain dLBTx4 and control cells and *E. coli* lpp-ompA-dLBTx8 and control cells were used at a density of $8\times10^8$ cells/ml. Where indicated, $CaCl_2$ was added at 100 mM. For *E. coli* cells, lpp-ompA-dLBTx8 expression was induced with 0.002% arabinose for 3 hr prior to performing adsorption experiments. Control cells contained the lpp-ompA-dLBTx8 expression construct but were not treated with arabinose. After a 20 min or 30 min incubation with 1.5 ml leachate, the supernatant was collected following centrifugation as described above and the metals remaining in the solution were quantified by ICP-MS. Y, La, Ce, and Nd, the most prevalent REE in the leachates, were quantified by ICP-MS.

It was found that phosphate reduced REE adsorption capacity (FIG. 8), likely due to the formation of insoluble REE phosphate phases. Firsching, F. H. et al., *J. Chem. Eng. Data* 1991, 36 (1) 93-95; Fujita, Y. et al., *Environ. Sci. Technol.* 2015, 49 (16) 9460-8. For the predominant four REEs in the leachate (Y, La, Ce, Nd), dLBTx4 outperformed the control cells, even without exogenous $Ca^{2+}$ supplementation (Table 4). As expected, although the total amount of the REE adsorption decreased with $Ca^{2+}$ addition, the relative disparity in adsorption between dLBTx4 and control cells was enhanced by 100 mM $Ca^{2+}$ addition (Table 4), consistent with reduced REE binding to the cell wall (FIG. 2C). Furthermore, as expected, dLBTx4 cells exhibited preferential adsorption of $Nd^{3+}$, $Y^{3+}$, and $Ce^{3+}$ over $La^{3+}$ (apparent in the presence of excess $Ca^{2+}$; Table 4). Together, these data demonstrate the utility of LBT-displayed cells for REF extraction from minimally processed source materials.

TABLE 4

REE Adsorbed from the Acid Leachate of Soil Samples from the Bull Hill Mine

| Sample | Y (µM) | La (µM) | Ce (µM) | Nd (µM) |
|---|---|---|---|---|
| Bull Hill leachate[a] | 1.1 (0.1)[b] | 15.9 (1.2) | 19.4 (2.1) | 15.3 (1.7) |
| control | 0.4 (0.0) | 5.8 (1.05) | 9.4 (0.3) | 7.8 (0.2) |
| dLBTx4 | 0.8 (0.0) | 10.9 (0.4) | 14.7 (0.3) | 12.1 (0.2) |
| control + 100 mM $CaCl_2$ | 0.1 (0.0) | 1.3 (0.1) | 3.5 (0.1) | 3.0 (0.2) |
| dLBTx4 + 100 mM $CaCl_2$ | 0.4 (0.0) | 3.5 (0.6) | 7.7 (0.9) | 6.7 (0.7) |

[a]Soluble REE concentrations after acid dissolution and pH adjustment to 6.0.
[b]Numbers in parentheses represent standard deviations of 3 replicates.

Figure 9A:
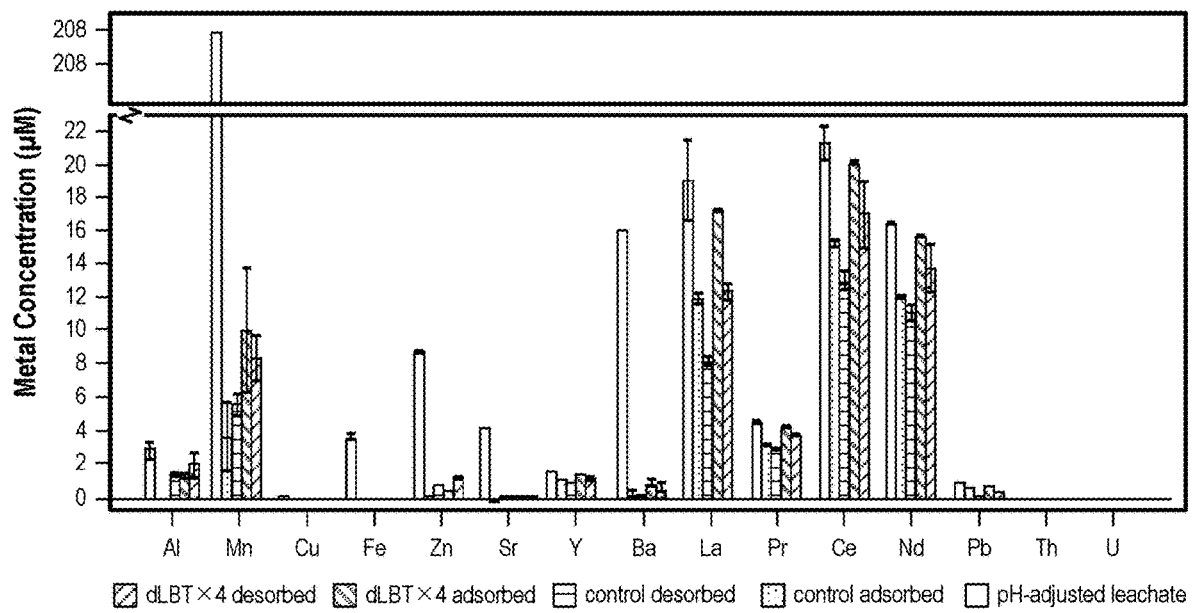
FIGS. 9A-9B show extraction of REEs from acid leachates of Bull Hill ore samples. Depicts the concentrations of metal adsorbed and desorbed from the Bull Hill leachates using *C. crescentus* (FIG. 9A; DMP146) and *E. coli* (FIG. 9B; DMP281) that were engineered to display multiple LBT copies on the cell surface. Adsorbed metal was calculated by subtracting the metal concentration remaining in solution after adsorption from the initial concentration in the pH-adjusted (6.0) Bull hill leachate ("pH-adjusted leachate"). Metal concentrations were determined using ICP-MS.
Figure 9B:
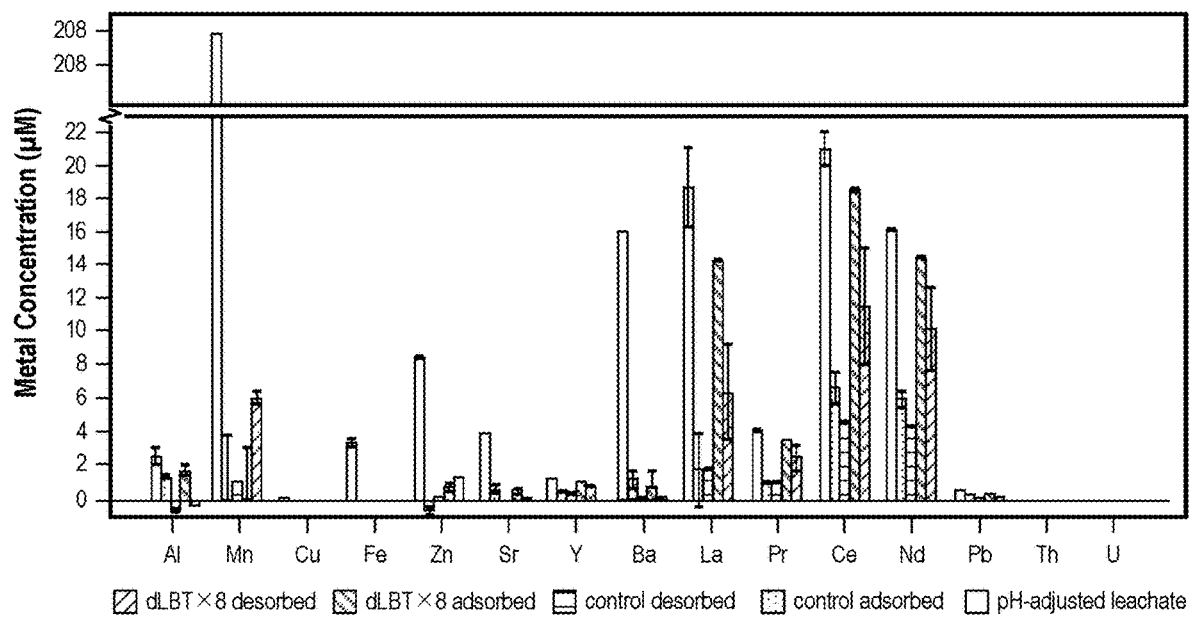

As shown in FIGS. 9A-9B, LBT-displayed *Caulobacter* (FIG. 9A) and *E. coli* (FIG. 9B) cells outperformed control cells, adsorbing greater than 75% of all REE present in the leachate. Very little adsorption was observed for the non-REE cations present in the leachate (Zn, Fe, Mn, Sr and Ba). The vast majority of REE adsorbed by *Caulobacter* and *E. coli* was desorbed using 5 mM citrate. Furthermore, the percentage of REE by weight of total metals in the eluent was greater than 90% for all samples compared to 30% in the initial leachate, highlighting the unique potential of the present bioadsorption technology to concentrate and enrich for REE from complex samples.

Figure 10A:
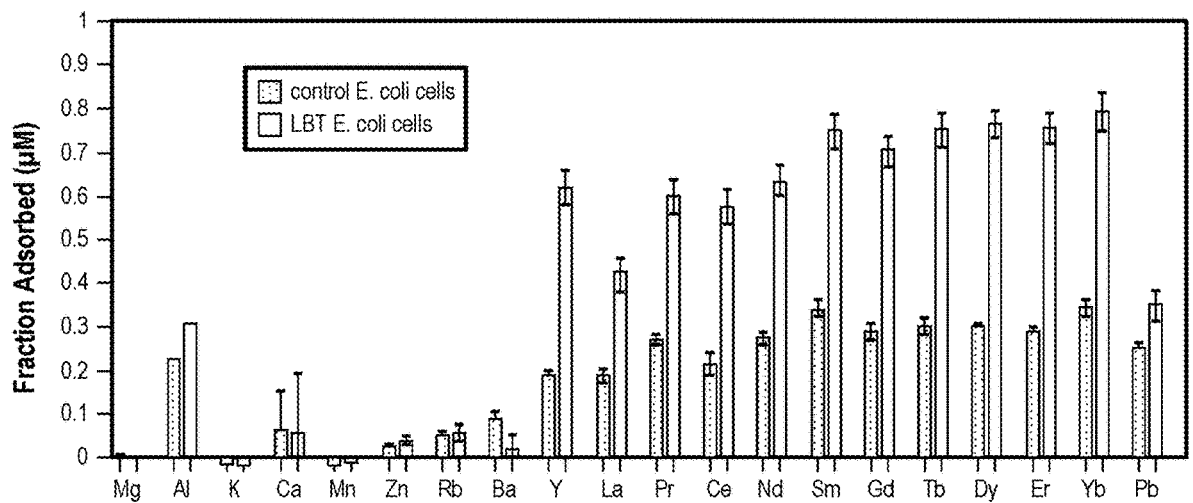
FIGS. 10A-10B show enrichment of REE elements from Round Top Mountain leachates.
Figure 10B:
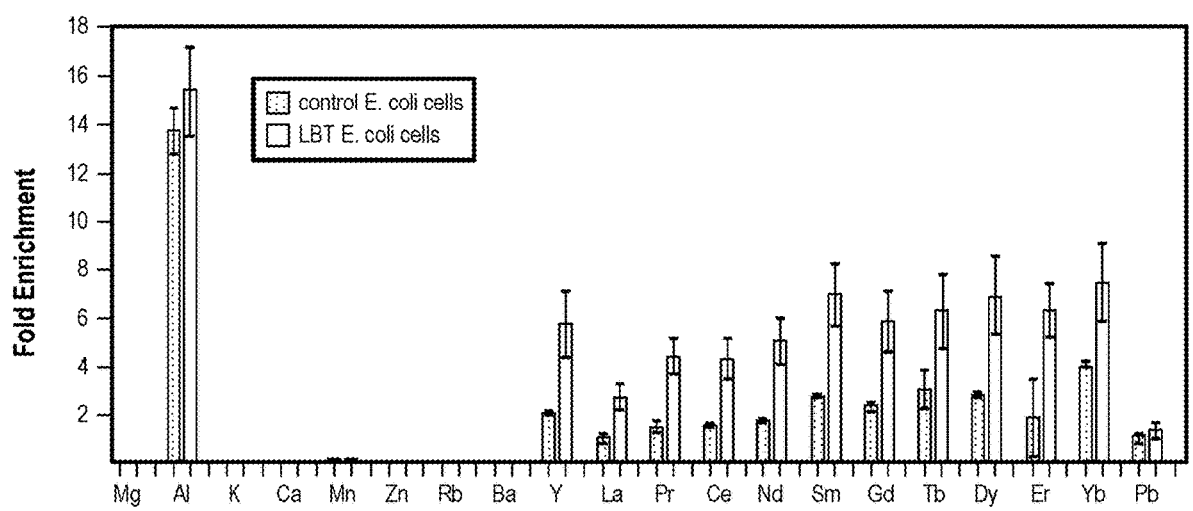
Figure 11A:
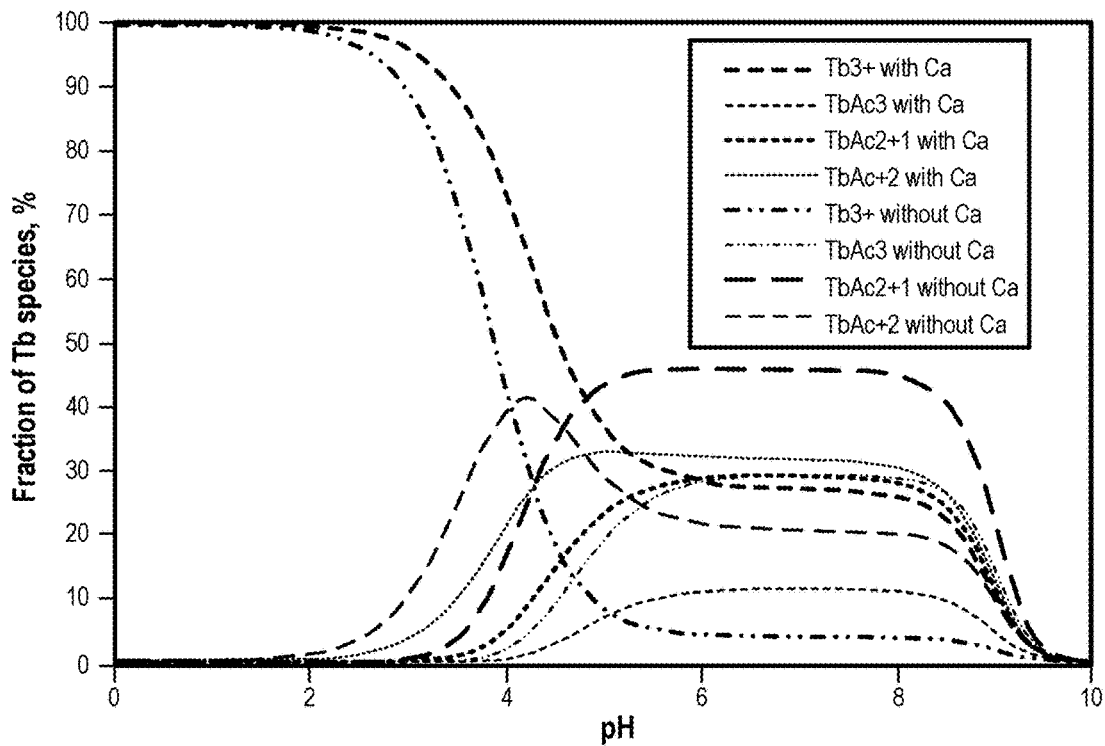
FIG. 11A demonstrates the relative amounts of Tb species in aqueous solution in the presence of 45 mM sodium acetate.
Figure 11B:
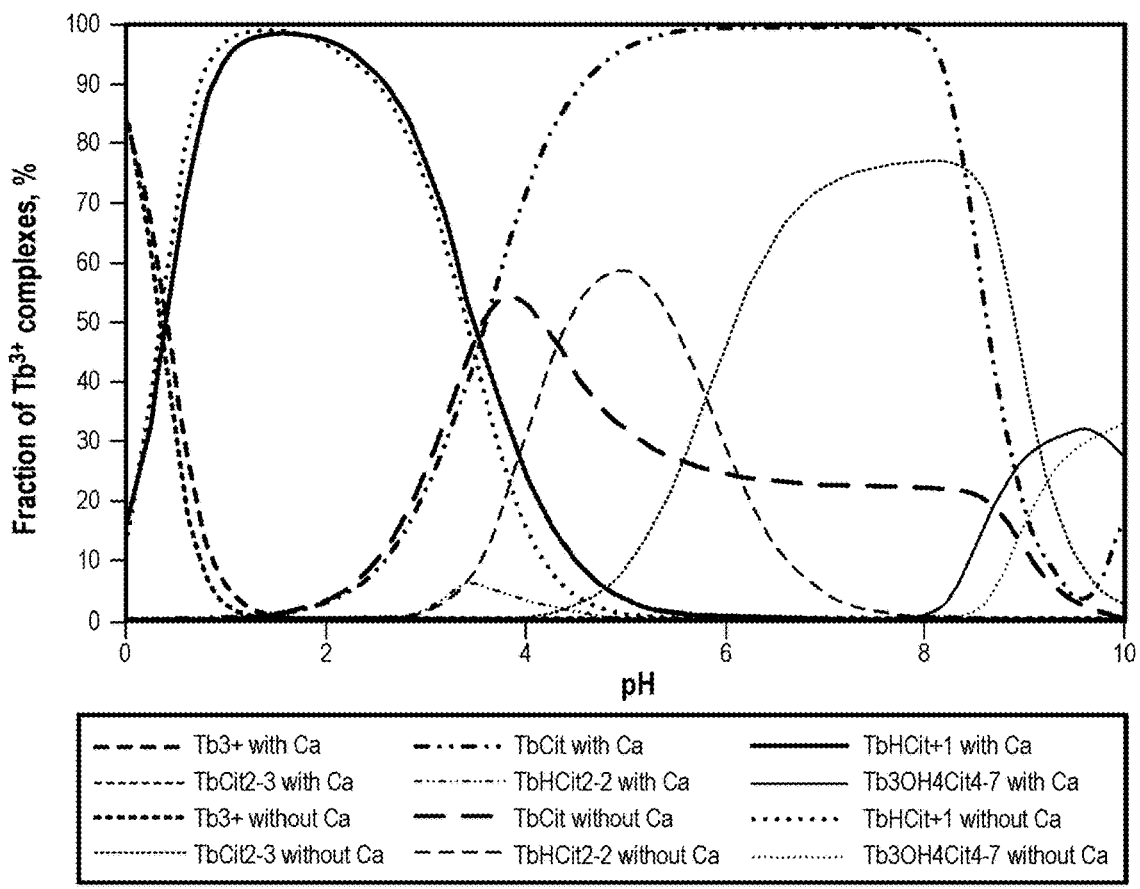
FIG. 11B demonstrates the relative amounts of Tb species in aqueous solution in the presence of 10 mM sodium citrate.

To further test the performance of the present bioadsorption technology, biosorption and desorption experiments were performed with the pH-adjusted acid leachate of an ore sample from Round Top Mountain (El Paso, Tex.) that contains REEs at less than 5% of the total metal weight. FIGS. 10A-10B. This sample is of particular interest as it contains a higher abundance of heavy rare earth elements relative to light REEs compared to most deposits. The data suggest that the LBT-displayed *E. coli* strain adsorbed 2-3 fold more REE compared to the control strain. FIG. 10A and FIG. 10B. This included adsorption of at least 60% of each REE with the exception of La that has weaker affinity for LBT. The best adsorbing non-REE metals were Al and Pb (10-20% of total Al and Pb), whereas Ca, Zn, Mg, Na, K, Mn, Rb and Ba were not adsorbed in appreciable quantities. Adsorbed REEs were eluted with 1/20 volume (relative to the volume of the leachate) to concentrate adsorbed metals REEs. The data revealed ~6-9-fold concentration of REEs with LBT-displayed cells. Consistent with the adsorption data, the vast majority of non-REE metals were below the detection limit of the ICP-MS. Aluminum was the only non-REE metal that was enriched by *E. coli* cells, with no significant difference observed between the LBT-displayed *E. coli* strain and the control. This suggests that Al was likely adsorbed to cell surface functional groups but not LBT. Overall, the data highlights the potential of LBT-displayed cells to enrich for REE from samples with low REE content (less than 5% of the initial metal content by weight was REE).

It is contemplated that the scalable and reusable bioadsorption platform for selective extraction of REEs developed in this study may prove particularly useful for REE extraction from waste streams with relatively low REE content (e.g., ore tailing, bauxite mine residues, phosphogypsum, incinerator ash, metallurgy slags, acid mine drainage, and industrial and municipal wastewaters). (Zhuang, W. Q., *Curr. Opin. Biotechnol.* 2015, 33, 327-335; Hennebel, T., *New Biotechnol.* 2015, 32 (1) 121-7; Binnemans, K. et al., *J. Cleaner Prod.* 2013, 51, 1-22; Lo, Y. C., *Bioresour. Technol.* 2014, 160, 182-190. Following a minimal solution conditioning (i.e., pH adjustment and potentially $Ca^{2+}$ addition), rapid, and reversible REE adsorption by LBT-displayed strains could enable a low cost and environmentally friendly alternative for REE extraction and processing.

Example 6: Generation of Genetically Engineered *Escherichia coli* Expressing Lanthanide Binding Tag To display LBT on the surface of *E. coli*, multiple, adjacent copies of LBT were fused to the 3' end of ompA (outer membrane protein A) and placed under the control of the arabinose-inducible promoter ($P_{BAD}$) as follows. Inserts containing 2, 4 and 8 copies of dLBT were prepared by a SpeI and PstI digest of p4ArsaA(723Δ)-dLBTx2, p4ArsaA(723Δ)-dLBTx4 and p4ArsaA(723Δ)-dLBTx8 (as described in detail above), respectively, and inserted using infusion cloning into the OmpA-PbrR and/or Lpp-OmpA-PbrR fusion protein expression plasmids (Wei, W. et al., *Environ. Sci. Technol.* 2014, 48, 3363-3371), which were linearized using the primers pBAD_infusionF (SEQ ID NO 10) and pBAD_infusionR (SEQ ID NO 11). The resulting ompA-LBT and lpp-ompA-LBT expression constructs were induced at mid-exponential phase using 0.002% Arabinose. After four hours of induction, the *E. coli* cells were harvested, washed once in 10 mM MES pH 6.0, and used in bioadsorption experiments.

Example 7: Biosorption Media for Rare Earth Extraction

The genetically engineered microbes discussed and described in detail above can be incorporated into various biosorption media (e.g., biofilm, microcapsules, and carbon nanotubes) for use in separating REEs from REE-containing mixed metal solutions.

The biolfilms (e.g., *Caulobacter* biofilm) described above will be used for REE adsorption and desportion cycles in continuous flow mode as shown in FIG. 12. Influent solution compositions for both adsorption and desorption as described above will be optimized. If in solution the materials can be used directly. If solids, acid and/or salt extraction (e.g., ion exchange) can be used to bring the REE into solution. Optimal conditions (e.g., temperature, pH, flow rate, addition of calcium) that maximize REE adsorption and recovery will also be determined. Varied temperature (e.g., ambient to 80° C.) flow experiments will test how temperature will affect biofilm stability and REE adsorption/desorption, while varied flow rate experiments will indicate how fluid exposure time affects REE adsorption and desorption. REE-LBT binding will be monitored by luminescence and inductively coupled plasma mass spectrometry (ICP-MS). At different times, sections of the biofilm will be cut out for biomass quantification (colony forming unit and microscopic numeration), REE quantification (ICP-MS) and structural analysis (REE uniformity by electron microscopy). Abiotic controls without biofilm attachment will be included to characterize the adsorption/desorption of REEs and other major metal ions on the supporting materials.

The genetically modified microbes provided herein may be encapsulated in both single and double emulsion modes (FIG. 14). Briefly, for double emulsion generation, the inner fluid is the bacterial suspension prepared at different wt % in saline buffer, encapsulated in the polymeric middle fluid. In single emulsion generation, the inner fluid is the bacterial suspension blended with polymer. Freeze-dried bacterial powders were mixed in water. Bacterial-loaded hydrogel capsules/particles were produced by adding 10 wt % UV-crosslinkable poly(ethylene glycol) diacrylate (PEGDA, MW=526 g/mol, Polysciences, Inc., Warrington, Pa.), 1 wt % crosslinker N,N'-methylene bisacrylamide (Sigma, St. Louis, Mo., USA), and also 1 wt % (2-hydroxide-4'-(2-hydroxymehoxy)-2-methylpropiophenone (Sigma, St. Louis, Mo.) as the photoinitiator in the polymer blend.

A three-input microcapillary device with hydrophobic or hydrophilic coatings that help drop generation was used, shown in FIG. 13. By controlling flow rates of each fluid, monodisperse drops were obtained near the entrance of the exit capillary. In order to harvest bacterial capsules/particles out of solution, UV exposure was applied to the generated drops to UV-crosslink PEGDA to help trap bacteria within the structure. Once fully crosslinked, bacterial particles were cleaned from the suspension by repeatedly replacing the continuous phase with copious amount of saline buffer before use for rare earth adsorption experiments.

During building of microfluidic device, the base was formed by bridging two 2 by 3 inch glass slides by epoxy and two small glass strips. A round glass capillary (15.24 cm long with an outer diameter of 1.0 mm and inner diameter of 0.580 mm, World Precision Instruments, Sarasota, Fla.) and a square capillary (with an internal width of 1.0 mm, VitroCom, Mountain Lakes, N.J.) compose the main components of the device. The square capillary is glued to the base after being cut to the desired length. The round capillary is centered in a pipette puller (Model P-97, Sutter Instruments, Novato, Calif.) to decrease its diameter in the center under tension and heat, breaking into two equally tapered capillaries. The tapered glass capillaries were then cleaved to the desired final diameters using a microforge station (Micro Forge MF 830, Narishige, Japan). Typical diameters of the input ($d_{input}$) and the exit ($d_{exit}$) capillaries ranged from 10 μm to 800 μm.

After cleaning in an ethanol solution with 10 minutes of sonication, tips were treated separately with different saline solutions to change the glass hydrophilicity and hydrophobicity. For example, for the double emulsion fabrication, the inner fluid capillary tip is treated to be hydrophobic so that the aqueous inner fluid could be easily repelled to break up into drops at the end of the capillary. Similarly, hydrophilic coating was applied to the exit capillary to accelerate the breakup of the oil-based middle fluid. Alternatively, for the single emulsion fabrication, both capillaries are treated with hydrophilic coating for easier breakup of the emulsion drops since here, the inner fluid will also be oil-based. These surface modifications are essential for stable emulsion drop formation.

The genetically modified microbes provided herein may be embedded into three-dimensional CNT/REE extraction membranes. Briefly, phosphate-buffered saline (PBS) solution is prepared by mixing sodium chloride (NaCl, 137 mmol/L), potassium chloride (KCl, 2.7 mmol/L), disodium hydrogen phosphate ($Na_2HPO_4$, 10 mmol/L), and potassium dihydrogen phosphate ($KH_2PO_4$, 1.8 mmol/L) in deionized water. Twenty mg carbon nanotube (CNT) powder and 8 mg sodium dodecylbenzenesulfonate (SDBS) are dispersed in 15 mL PBS solution. The solution mixture is then sonicated for 15 min at 300 W to ensure CNT are homogeneously dispersed in PBS solution. Approximately, 1 mL of REE bacteria suspension is added with controllable microbes concentration (e.g., $1\times10^{10}$ cells per mL) into the CNT solution. The solution mixture is then deposited onto the cellulose acetate filter (pore size 0.2 μm) through vacuum filtration. The CNT/bacteria membrane is rinsed with PBS solution to remove SDBS residues.

Example 8: Post-Processing and Recovery of Rare Earth Elements to Make Salable REE Oxides ICP-MS is used to measure the initial concentration of the component ions contained within a precursor solution containing REE trivalent ions chelated by citrate along with matrix mineral ions such as iron, copper, calcium, and the like. If the concentration of matrix mineral ions such as iron, copper, and calcium cannot be ignored, pH adjustment can be carried out to precipitate these non-REE ions. It was previously reported the non-REE matrix mineral ions could be largely removed through forming insoluble alkaline precipitate. For example, about 99.99% iron ions and 76.12% copper ions can be precipitated in the form of $Fe(OH)_3$ and $Cu(OH)_2$ at pH 4.97, while REE ions still remains stable. Parhi P. K., et al. (2015) *J Rare Earths* 33(2): 207-213. Increasing the pH can further boost the precipitation of the non-REE ions. Filtration can be performed to remove the matrix ion involved precipitate.

Precipitation by Oxalic acid: Oxalic acid is commonly used as the precipitant in recovering REE due to its high efficiency in producing insoluble RE oxalate. Chi R., et al. (1999) *Metall and Materi Trans B* 30(2):189-195. Previous studies have shown at pH 2 the recovery of REE through oxalate precipitation achieved a maximum with around 95% of REE recovered. Calcination of the obtained precipitate in air at 900° C. harnesses the final solids composed of REE oxides.

Evaporative Crystallization: The steps described above for removing matrix mineral ions are kept the same with the above method. The remaining solution that primarily contains REE based citrate is heated to vaporize the water and obtain the crystals. Thermal treatment can be done on the crystals (REE-citrate) to 800° C. reported previously to get solid REE oxide. Wu S., et al. (1995) *J Thermal Anal* 45(1):199-206. It is contemplated that one advantage of evaporative crystallization is a decrease in unexpected loss of rare earth element that may result from incomplete precipitation by oxalic acid.

Evaluation of REE Recovery: Any method to evaluate REE recovery can be used. For example, ICP-MS is usually used to measure the initial REE concentration and the residue concentration to get the efficiency of REE recovery. Thermogravimetry and differential scanning calorimetry (TGA-DSC) could be assisted to analyze the quantity composition of the final solids. X-ray diffraction can also be used to characterize the final composition of the solid.

Example 9: Biosensors for Rare Earth Detection

The unique photophysical and electronic properties of lanthanide ions, it is contemplated that lanthanide binding luminescent ligands described above can be used for rapid screening of REE enriched materials. Moore, E. G. et al., (2007) *Inorganic Chem* 46, 5468-5470; Daumann, L. J., (2016) *J Inorganic Biochem* 162, 263:273; Allen, K. N. et al., (2010) *Current Opinion in Chem Biol* 14, 247-254; Franz, K. J., (2003) *Chem Bio Chem* 4, 265-271. Use of field-deployable sensors or test kits based on such mechanisms will be useful for detection of REE in coal or coal byproducts sensors, monitoring of REE content in process streams, detection of upsets during industrial processing, and rapid testing and validation of new extraction or separation techniques.

REE are key components of modern electronics and clean energy technologies, and because of anticipated supply risks, global interest in REE recycling and recovery from non-traditional, low-grade sources is increasing. Potential sources that have gained attention include coal and associated byproducts such as ash. Gomes, H I, et al. (2016) *J Clean Prod.* 112:3571-3582; Taggart, R. K., (2016) *Environ. Sci. Technol.* 50, 5919-5926. However, determination of whether a material contains economic REE content is challenging. X-ray fluorescence (XRF) can be used to detect surface or near surface REE in solids (Towett, E. K. et al., (2013) *Science of The Total Environment* 463-464, 374-388), but is likely not sensitive enough for metals at the concentrations expected in coal and coal byproducts. Inductively Coupled Plasma-Mass Spectrometry or colorimetric assays (Onishi, H. et al., (1972) *Talanta* 19, 473-478) can be used REE detection and quantification of REE present in liquid form, but these techniques are expensive and or not readily amenable for field deployment in a portable instrument or assay. The availability of a simple and rapid REE detection method could significantly reduce the cost of REE prospecting, by providing an initial screening result that if promising could then be followed up by additional sampling and analysis.

Complexation of lanthanides by peptides coupled with the unique spectroscopic properties of lanthanides (Taggart, R. K., (2016) *Environ. Sci. Technol.* 50, 5919-5926) is the underpinning for luminescent applications of lanthanide binding tags (LBT), originally invented as biochemical tools for the study of proteins (Daumann, L. J., (2016) *J Inorganic Biochem* 162, 263:273). A peptide sequence specifically designed to bind lanthanides includes amino acids which have chromophore side-chains (tyrosine or tryptophan), and upon lanthanide binding the complex exhibits unique luminescence properties, enabling detection/visualization. To date, LBTs have primarily been used with Tb because it exhibits particularly long-lived luminescence, but Eu also exhibits appropriate luminescent properties (Towett, E. K. et al., (2013) *Science of The Total Environment* 463-464, 374-388). In REE-containing samples, although specific lanthanide enrichments may vary by provenance, generally the whole lanthanide series is present (Taggart, R. K., (2016) *Environ. Sci. Technol.* 50, 5919-5926). Thus a positive signal generated upon exposure of a sample to the specialized REE ligand would imply that the sample is enriched with REE including Tb or Eu, and is worthy of further examination.

The genetically engineered microbe discussed and described in detail above are advantageous for use as sensing technologies for REE given that immobilization and/or concentration of the REE-ligand complex offers a way of enhancing the signal strength. In dilute solution, the ligands can undergo dynamic intra-molecular rotation, resulting in non-radiative relaxation and energy loss. In aggregated or immobilized systems, the physical constraints suppress the intra-molecular rotation and more of the excitation energy can be conserved and transferred to the Tb or Eu, resulting in increased luminescence. Development of methods to immobilize the chromophore ligand also enables the future development of real-time in-line sensors. It is contemplated that producing the LBT in high density on bacterial surface (e.g., by anchoring onto S-layer or OmpA) such that the LBT are in close proximity. Furthermore, to eliminate potential luminescence interference from the native bacterial surface, S-layers can be subsequently stripped from the cells without affecting binding properties. The candidate ligands can also be attached to various solid surfaces utilizing commercially available systems (e.g., carboxylic acid functionalized beads or prefunctionalized glass slides).

From the foregoing, it will be appreciated that specific embodiments of the invention have been described herein for purposes of illustration, but that various modifications may be made without deviating from the scope of the invention. Accordingly, the invention is not limited except as by the appended claims.

The invention claimed is:

1. A genetically engineered microbe comprising an exogenous nucleic acid sequence encoding a rare earth element (REE) binding ligand, wherein the REE binding ligand comprises more than 6 copies of double lanthanide binding tags (dLBTs) connected by a flexible and hydrophilic linker.

2. The microbe of claim 1, wherein the microbe is a bacterium or bacteriophage.

3. The microbe of claim 2, wherein the bacterium is selected from the group consisting of *Caulobacter crescentus* (*C. crescentus*), *Escherichia coli* (*E. coli*), and *Lactobacillus*.

4. The microbe of claim 1, wherein the REE binding ligand is expressed on the cell surface and/or within a cell surface protein.

5. The microbe of claim 4, wherein the REE binding ligand is displayed on the cell surface by a surface layer (S-layer) protein.

6. The microbe of claim 5, wherein the dLBTs are functionalized to an outer membrane protein A (OmpA).

7. The microbe of claim 1, wherein the dLBTs on the cell surface protein comprise 8 copies of the dLBTs.

8. The microbe of claim 1, wherein a binding affinity (Ka) of the REE binding ligand of the microbe to a REE is between about 1 μM and 200 μM.

9. The microbe of claim 1, wherein efficacy of REE adsorption by the microbe is 2-fold or greater increase compared to a nonengineered control.

10. The microbe of claim 1, wherein the REE binding ligand binds a REE selected from the group consisting of lanthanum (La), cerium (Ce), praseodymium (Pr), neodymium (Nd), promethium (Pm), samarium (Sm), europium (Eu), gadolinium (Gd), terbium (Tb), dysprosium (Dy), holmium (Ho), erbium (Er), thulium (Tm), ytterbium (Yb), lutetium (Lu), scandium (Sc) and yttrium (Y).

11. The microbe of claim 1, wherein the microbe has a preferential binding affinity for a smaller atomic radii REE selected from the group consisting of gadolinium, terbium, dysprosium, holmium, erbium, europium, ytterbium, and yttrium.

12. The microbe of claim 11, wherein the microbe has a preferential binding affinity for a smaller atomic radii REE compared to a larger atomic radii REE, wherein the smaller atomic radii REE is selected from the group consisting of terbium, dysprosium, erbium, europium, and ytterbium, and
   wherein the larger atomic radii REE is selected from the group consisting of lanthanum, cerium, and praseodymium.

13. A composition comprising an amount of the genetically engineered microbe of claim 1.

14. A system comprising an amount of the genetically engineered microbe of claim 1.

15. The system of claim 14, wherein the genetically engineered microbes are attached to a solid support.

16. The system of claim 15, wherein the solid support comprises a column, a membrane, or a bead.

17. A method for extracting rare earth elements (REE) from a material comprising the steps of:
   (a) providing the genetically engineered microbe of claim 1;
   (b) contacting the genetically engineered microbe with a REE containing material, whereupon the REE binding ligand specifically binds at least a portion of the REE to form a microbe-REE complex;
   (c) separating the microbe-REE complex from at least a portion of the material; and
   (d) separating the REE from the genetically engineered microbe to produce regenerated genetically engineered microbes.

18. The method of claim 17, wherein the material is rare earth ores, geothermal brines, coal, coal byproducts, mine tailings, phosphogypsum, and/or acid or salt leachate of solid materials.

19. The method of claim 17, further comprising reusing the regenerated genetically engineered microbes of step (d) to carry out steps (a)-(c).

* * * * *

SEQUENCE LISTING

<160> NUMBER OF SEQ ID NOS: 11

<210> SEQ ID NO 1
<211> LENGTH: 24
<212> TYPE: DNA
<213> ORGANISM: Artificial Sequence
<220> FEATURE:
<223> OTHER INFORMATION: Primer

<400> SEQUENCE: 1
tttatcgata ccaacaacga tggc                                    24

<210> SEQ ID NO 2
<211> LENGTH: 16
<212> TYPE: DNA
<213> ORGANISM: Artificial Sequence
<220> FEATURE:
<223> OTHER INFORMATION: Primer

<400> SEQUENCE: 2
tgccagcagt tcgtcg                                             16

<210> SEQ ID NO 3
<211> LENGTH: 34
<212> TYPE: DNA
<213> ORGANISM: Artificial Sequence
<220> FEATURE:
<223> OTHER INFORMATION: Primer

<400> SEQUENCE: 3
gacgaactgc tggcatctgc agatggatcc gtcg                          34

<210> SEQ ID NO 4
<211> LENGTH: 33
<212> TYPE: DNA
<213> ORGANISM: Artificial Sequence
<220> FEATURE:
<223> OTHER INFORMATION: Primer

<400> SEQUENCE: 4
gttggtatcg ataaaagatc tggatccgtc gcc                           33

<210> SEQ ID NO 5
<211> LENGTH: 32
<212> TYPE: PRT
<213> ORGANISM: Artificial Sequence
<220> FEATURE:
<223> OTHER INFORMATION: Synthetically generated sequence

<400> SEQUENCE: 5

Phe Ile Asp Thr Asn Asn Asp Gly Trp Ile Glu Gly Asp Glu Leu Phe
1               5                   10                  15

Ile Asp Thr Asn Asn Asp Gly Trp Ile Glu Gly Asp Glu Leu Leu Ala
            20                  25                  30

<210> SEQ ID NO 6
<211> LENGTH: 96
<212> TYPE: DNA
<213> ORGANISM: Artificial Sequence
<220> FEATURE:
<223> OTHER INFORMATION: Synthetically generated sequence

<400> SEQUENCE: 6
tttatcgata ccaacaacga tggctggatc gaaggtgacg aactgttcat tgataccaac     60
aacgacggct ggatcgaagg cgacgaactg ctggca                              96

<210> SEQ ID NO 7
<211> LENGTH: 441
<212> TYPE: DNA
<213> ORGANISM: Artificial Sequence
<220> FEATURE:
<223> OTHER INFORMATION: Synthetically generated sequence

<400> SEQUENCE: 7
tatttcctca agtgacggga tgccgctatt gagtatgcaa aaagatctac tagttttatc     60
gataccaaca acgatggttg gatcgagggt gacgaactgt ttatcgacac gaataatgac    120
ggttggattg agggtgacga actgctggca gctagtccgc ccgcgcacgg ggtgaccagc    180
gcgccggata cccgccccgc ccccggttcg acggctagtt tcatcgacac caacaatgat    240
ggctggatcg aaggcgacga gctgttcatt gataccaata acgacggctg gatcgaaggc    300
gacgaactgc tggcagctag tccgcccgcc cacggcgtga cctcggcgcc ggacacgcgc    360
cccgccccgg tagcaccgc tagcgctgca gaaacttctc aactttcaac tctttcgcca    420
acggaactgg agtcgttaag c                                              441

<210> SEQ ID NO 8
<211> LENGTH: 679
<212> TYPE: DNA

<213> ORGANISM: Artificial Sequence
<220> FEATURE:
<223> OTHER INFORMATION: Synthetically generated sequence

<400> SEQUENCE: 8

| | |
|---|---|
| agatctacta gttttatcga taccaacaac gatggttgga tcgagggtga cgaactgttt | 60 |
| atcgacacga ataatgacgg ttggattgag ggtgacgaac tgctggcagc tagtccgccc | 120 |
| gcgcacgggg tgaccagcgc gccggatacc cgccccgccc ccggttcgac ggctagtttc | 180 |
| atcgacacca acaatgatgg ctggatcgaa ggcgacgagc tgttcattga taccaataac | 240 |
| gacggctgga tcgaaggcga cgaactgctg gcagctagtc cgcccgccca cggcgtgacc | 300 |
| tcggcgccgg acacgcgccc cgccccgggt agcaccgcta gttttatcga taccaacaac | 360 |
| gatggttgga tcgagggtga cgaactgttt atcgacacga ataatgacgg ttggattgag | 420 |
| ggtgacgaac tgctggcagc tagtccgccc gcgcacgggg tgaccagcgc gccggatacc | 480 |
| cgccccgccc ccggttcgac ggctagtttc atcgacacca acaatgatgg ctggatcgaa | 540 |
| ggcgacgagc tgttcattga taccaataac gacggctgga tcgaaggcga cgaactgctg | 600 |
| gcagctagtc cgcccgccca cggcgtgacc tcggcgccgg acacgcgccc cgccccgggt | 660 |
| agcaccgcta gcgctgcag | 679 |

<210> SEQ ID NO 9
<211> LENGTH: 1339
<212> TYPE: DNA
<213> ORGANISM: Artificial Sequence
<220> FEATURE:
<223> OTHER INFORMATION: Synthetically generated sequence

<400> SEQUENCE: 9

| | |
|---|---|
| agatctacta gttttatcga taccaacaac gatggttgga tcgagggtga cgaactgttt | 60 |
| atcgacacga ataatgacgg ttggattgag ggtgacgaac tgctggcagc tagtccgccc | 120 |
| gcgcacgggg tgaccagcgc gccggatacc cgccccgccc ccggttcgac ggctagtttc | 180 |
| atcgacacca acaatgatgg ctggatcgaa ggcgacgagc tgttcattga taccaataac | 240 |
| gacggctgga tcgaaggcga cgaactgctg gcagctagtc cgcccgccca cggcgtgacc | 300 |
| tcggcgccgg acacgcgccc cgccccgggt agcaccgcta gttttatcga taccaacaac | 360 |
| gatggttgga tcgagggtga cgaactgttt atcgacacga ataatgacgg ttggattgag | 420 |
| ggtgacgaac tgctggcagc tagtccgccc gcgcacgggg tgaccagcgc gccggatacc | 480 |
| cgccccgccc ccggttcgac ggctagtttc atcgacacca acaatgatgg ctggatcgaa | 540 |
| ggcgacgagc tgttcattga taccaataac gacggctgga tcgaaggcga cgaactgctg | 600 |
| gcagctagtc cgcccgccca cggcgtgacc tcggcgccgg acacgcgccc cgccccgggt | 660 |
| agcaccgcta gttttatcga taccaacaac gatggttgga tcgagggtga cgaactgttt | 720 |
| atcgacacga ataatgacgg ttggattgag ggtgacgaac tgctggcagc tagtccgccc | 780 |
| gcgcacgggg tgaccagcgc gccggatacc cgccccgccc ccggttcgac ggctagtttc | 840 |
| atcgacacca acaatgatgg ctggatcgaa ggcgacgagc tgttcattga taccaataac | 900 |
| gacggctgga tcgaaggcga cgaactgctg gcagctagtc cgcccgccca cggcgtgacc | 960 |
| tcggcgccgg acacgcgccc cgccccgggt agcaccgcta gttttatcga taccaacaac | 1020 |
| gatggttgga tcgagggtga cgaactgttt atcgacacga ataatgacgg ttggattgag | 1080 |
| ggtgacgaac tgctggcagc tagtccgccc gcgcacgggg tgaccagcgc gccggatacc | 1140 |
| cgccccgccc ccggttcgac ggctagtttc atcgacacca acaatgatgg ctggatcgaa | 1200 |

```
ggcgacgagc tgttcattga taccaataac gacggctgga tcgaaggcga cgaactgctg      1260
gcagctagtc cgcccgccca cggcgtgacc tcggcgccgg acacgcgccc cgccccgggt      1320
agcaccgcta gcgctgcag                                                   1339

<210> SEQ ID NO 10
<211> LENGTH: 37
<212> TYPE: DNA
<213> ORGANISM: Artificial Sequence
<220> FEATURE:
<223> OTHER INFORMATION: Primer

<400> SEQUENCE: 10
tatcgataaa actagtggat cctccgttgt ccggacg                                37

<210> SEQ ID NO 11
<211> LENGTH: 45
<212> TYPE: DNA
<213> ORGANISM: Artificial Sequence
<220> FEATURE:
<223> OTHER INFORMATION: Primer

<400> SEQUENCE: 11
tagcaccgct agcgctgcac tcgaggatta caaggatgac gacga                       45
```